United States Patent [19]
Tatsuno et al.

[11] Patent Number: 6,080,101
[45] Date of Patent: Jun. 27, 2000

[54] ENDOSCOPE VIDEO CAMERA HEAD WHICH CAN BE AUTOCLAVED

[75] Inventors: Yutaka Tatsuno, Sagamihara; Fuminori Tanahashi, Hachioji, both of Japan

[73] Assignee: Olympus Optical Co. Ltd., Japan

[21] Appl. No.: 09/140,808

[22] Filed: Aug. 26, 1998

[51] Int. Cl.[7] .................................................. A61B 1/04
[52] U.S. Cl. ...................... 600/112; 600/109; 600/110; 600/122; 600/133; 600/134; 348/65
[58] Field of Search ................................. 600/109, 110, 600/112, 122, 133, 134; 348/65, 73, 75

[56] References Cited

U.S. PATENT DOCUMENTS

| | | | |
|---|---|---|---|
| 4,993,405 | 2/1991 | Takamura et al. | 600/110 |
| 5,587,736 | 12/1996 | Walls . | |
| 5,599,278 | 2/1997 | Hibbard | 600/133 |
| 5,609,561 | 3/1997 | Uehara et al. | 600/112 |
| 5,868,664 | 2/1999 | Speier et al. | 600/112 |

FOREIGN PATENT DOCUMENTS

| | | |
|---|---|---|
| 5-32822 | 8/1993 | Japan . |
| 7-39515 | 2/1995 | Japan . |
| 7-100102 | 4/1995 | Japan . |
| 7-100104 | 4/1995 | Japan . |

*Primary Examiner*—Linda C. M. Dvorak
*Assistant Examiner*—Brad C. Blaise
*Attorney, Agent, or Firm*—Ostrolenk, Faber, Gerb & Soffen, LLP

[57] ABSTRACT

A TV camera is attached to an eyepiece unit of an endoscope and includes a solid-state imaging device. A housing of the TV camera has an outer metallic sheathing. The outer metallic sheathing is hermetically coupled via an insulating material to a metallic housing frame of an electric connector which has contact pins connected to the solid-state imaging device and which is fixed hermetically using a hermetic seal. This structure defines a hermetically enclosed space which can withstand autoclaving. A shielding sheathing layer is formed inside an insulating layer within the hermetic space in order to shield an electric circuit including the solid-state imaging device and which is located inside the shielding sheathing layer. The shielding sheathing layer is designed to communicate with the housing metallic frame of the connector that is isolated and sheathed. This structure provides measures for solving problems concerning electromagnetic compatibility (EMC).

11 Claims, 24 Drawing Sheets

ENDOSCOPE VIDEO CAMERA HEAD WHICH CAN BE AUTOCLAVED

BACKGROUND OF THE INVENTION

1. Field of the Invention

The present invention relates to an endoscopic imaging apparatus being mounted on an endoscope, having an outer metallic sheathing thereof coupled hermetically to a housing frame of a connector via an insulating hermetic member, having a shielded solid-state imaging device stowed in an internal hermetic space, and being capable of being autoclaved.

2. Description of the Related Art

An endoscopic imaging apparatus mounted on an endoscope to be inserted into a body cavity and having an imaging device incorporated therein is an electrical equipment whose electrical safety is guaranteed. A patient circuit (or an equivalent) is isolated from a housing metallic member.

In recent years, there has been concern about the environment; therefore, it has become increasingly desirable to be able to autoclave an endoscopic imaging apparatus under high-temperature and high-pressure steam without the use of any additional agents.

For example, Japanese Unexamined Patent Publication No. 7-100104 or 7-100102 has disclosed an endoscopic imaging apparatus capable of being autoclaved. In this prior art, a camera head is formed with a three-layered sheathing member composed of a metallic layer, insulating layer, and conductive layer in that order from the outside and is thus structured to be adiabatic.

In the camera head capable of being autoclaved, a housing thereof is structured to be hermetically sealed. In this case, the housing is made of a metal selected upon consideration of its heat resistance, steam resistance, and coefficient of thermal expansion.

In practice, care must be taken upon use of a cautery knife and to provide a guarantee of safety. For an endoscopic imaging apparatus including an electrical circuit, therefore, a structure of isolating the internal circuit from a housing of a camera head in order to ensure isolation from a rigid endoscope with a metallic housing is usually adopted.

Moreover, a patient circuit (or an equivalent) must be provided with a shielding structure having a potential of 0 V in order to solve a problem arising from coping with electromagnetic interference or from ensuring electromagnetic compatibility (EMC).

Consequently, the patient circuit (or an equivalent) and metallic housing must be isolated from each other. Moreover, they must be sealed hermetically. Conventionally, airtightness is attained using an adhesive or the like. The thus attained airtightness is deteriorated by steam.

SUMMARY OF THE INVENTION

An object of the present invention is to provide an endoscopic imaging apparatus capable of solving the problems arising from coping with electromagnetic interference, hermetically sealing an insulating structure and metal structures, and autoclaving the apparatus.

Another object of the present invention is to provide an endoscopic imaging apparatus that will not be damaged or deteriorated in optical performance because of changes in the ambient temperature occurring during autoclaving or the like.

An endoscopic imaging apparatus of the present invention is attached to an endoscope directly or via an adapter, and has hermetically sealed imaging optical system which includes at least a solid-state imaging device.

The endoscopic imaging apparatus includes an outer metallic sheathing that forms a hermetic sealing member in cooperation with an optical member, an internal shielding sheathing for shielding the solid-state imaging device, and an inner insulating layer interposed between the outer metallic sheathing and internal shielding sheathing.

A hermetic coupling means is included for hermetically coupling the internal shielding sheathing to a frame of a hermetic connector spliced to a shielding sheath of a cable while conductivity is maintained. The hermetic coupling means is also used to hermetically couple the outer metallic sheathing to the internal shielding sheathing via an insulator. The solid-state imaging device is shielded by a shielding means. Consequently, the problem arising in coping with electromagnetic interference can be solved. Moreover, the insulator and metal are hermetically sealed so that they an be autoclaved.

BRIEF DESCRIPTION OF THE DRAWINGS

FIGS. 1 to 3B relate to a first embodiment of the present invention;

FIG. 1 is a diagram showing an overall configuration of an endoscope system including a first embodiment of the present invention;

FIG. 2 is a sectional view showing a structure of a TV camera of the first embodiment;

FIG. 3B is an enlarged sectional view of a portion in which an insulator is used for hermetic coupling;

FIG. 4 is a sectional view showing the structure of a TV camera of the second embodiment;

FIG. 5 is a sectional view showing portions of first and second connectors that are attached to each other;

FIG. 6 is an enlarged sectional view of a portion in which an insulator is used for hermetic coupling in a variant of the second embodiment;

FIGS. 10 to 12 relate to a fourth embodiment of the present invention;

FIG. 10 is a sectional view showing the structure of an optical adapter and its surroundings in the fourth embodiment;

FIG. 12 is a sectional view showing a deaeration bore to be sealed with a sealing material;

FIG. 13 is a sectional view showing a camera head of the first variant;

FIG. 14 is an enlarged view of a distal portion of the camera head shown in FIG. 13;

FIG. 21 is a sectional view of a disassembled state of a camera head of the seventh embodiment;

FIG. 22 is a sectional view of a connected state of the camera head;

DESCRIPTION OF THE PREFERRED EMBODIMENTS

Figure 1:
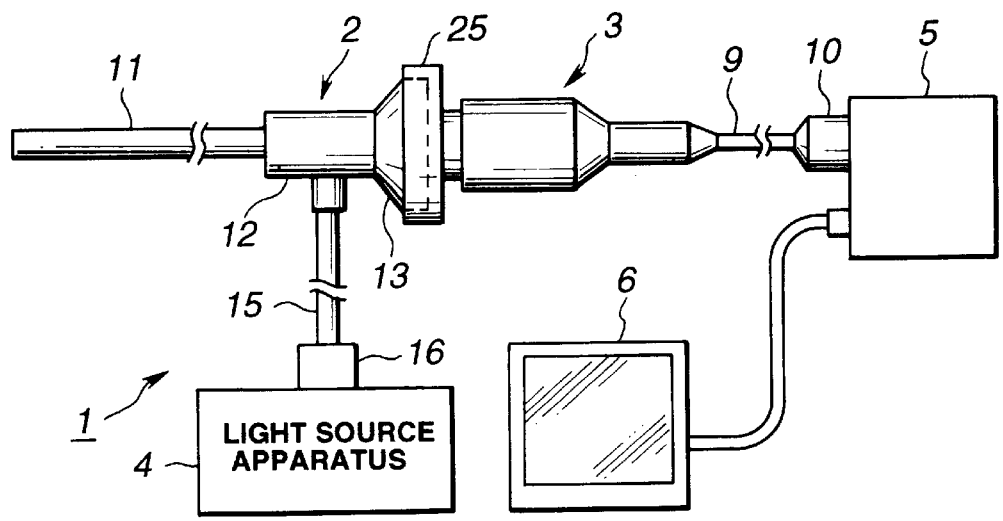
Figure 2:
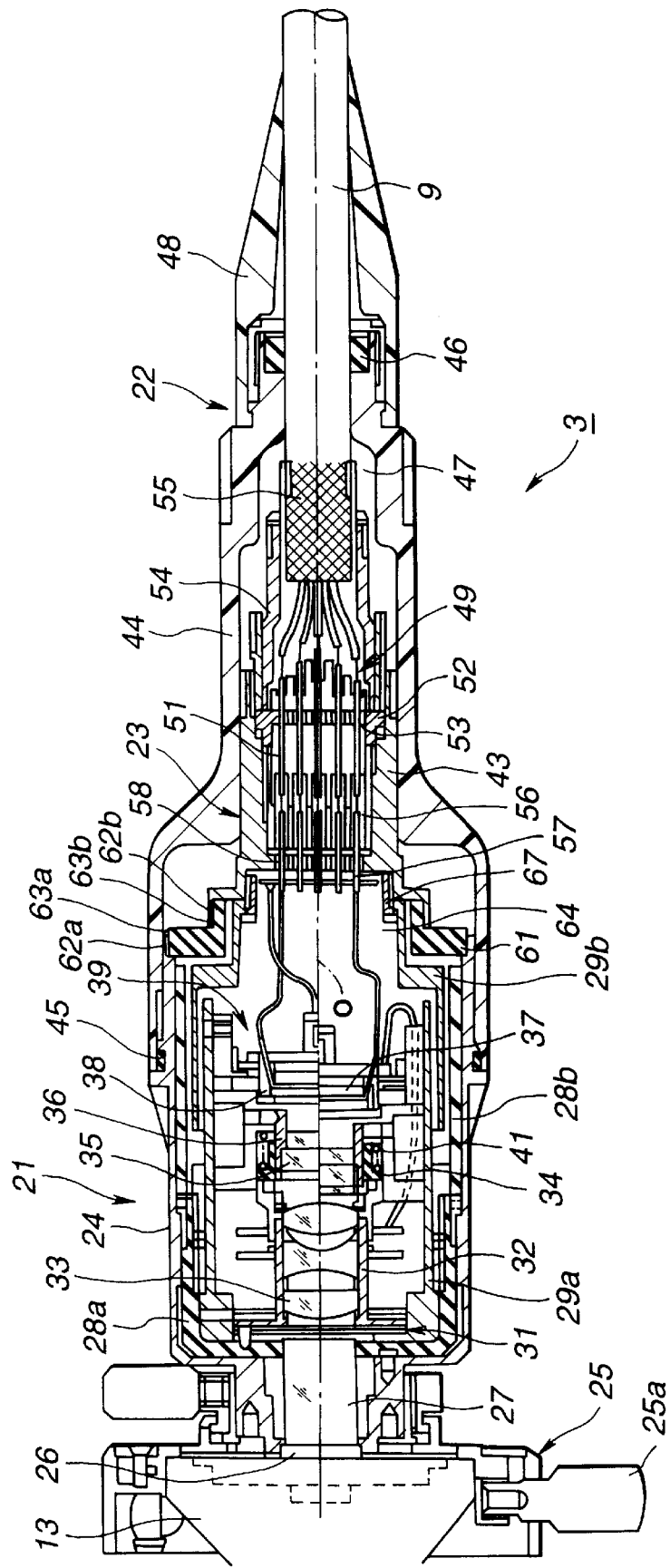

Referring to FIGS. 1 to 3, a first embodiment of the present invention will be described below.

An endoscope system 1 shown in FIG. 1 comprises a rigid endoscope 2, a TV camera 3 serving as an endoscopic imaging apparatus and being mounted on the rigid endoscope 2 so that it can be dismounted freely, a light source apparatus 4 for supplying illumination light to the rigid endoscope 2, a camera control unit (hereinafter CCU) 5 for processing a signal sent from the TV camera 3, and a monitor 6 for displaying an image represented by a video signal output from the CCU 5.

The rigid endoscope 2 includes an elongated rigid insertion unit 11, a large-diameter hand-held unit 12 communicating with the back end of the insertion unit 11, an eyepiece unit 13 formed at the back end of the hand-held unit 12, and a base formed on the lateral surface of the hand-held unit 12. A light guide cable 15 is coupled to the base. A connector 16 spliced to the terminal of the light guide cable 15 can be coupled to the light source apparatus 4 so that it can be uncoupled freely.

When the connector 16 of the light guide cable 15 is coupled to the light source apparatus 4, white light emanating from a lamp, which is not shown, in the light source apparatus 4 is irradiated to the end surface of the light guide. Illumination light propagated by the light guide is supplied to a light guide extending through the rigid endoscope 2, and emitted forward through an illumination window in the distal part of the insertion unit 11. An object is then illuminated.

An image of the object illuminated with the illumination light emitted through the illumination window is formed by an objective, which is not shown, included in the distal part. The formed image is transmitted to an eyepiece unit 13 by a relay optical system. Thus, the image can be viewed an enlargement through an eyepiece.

A mount 25 of the TV camera 3 is freely detachably attached to the eyepiece unit 13. The TV camera 3 has a charge-coupled device (hereinafter CCD) 37 (FIG. 2) serving as an imaging means incorporated therein. The CCD 37 is connected to the CCU 5 through a connector 10, which can be coupled to the CCU 5 in a freely detachable manner, over (a signal line of) a camera cable 9 extending from the TV camera 3.

A CCD driving signal sent from a CCD driver, which is not shown, in the CCU 5 is transmitted over the camera cable 9 to the CCD 37. A signal which has been photoelectrically converted by the CCD 37 is then read. The signal is sent to a video signal generation circuit, which is not shown, in the CCU 5, whereby a video signal is generated. Consequently, an object image is displayed on the display surface of the monitor 6.

As will be described later, the CCD 37 is located inside an internal shielding layer for shielding the TV camera 3. The shielding layer is structured to block electromagnetic waves. Specifically, the shielding layer is connected to a ground at which potential is 0 V, in the CCU 5 through a housing member of a connector shielded with an external insulating member and a shield inside an armor of the camera cable 9. Consequently, the strength of a signal component radiated externally as noise from the CCD 37 or over a signal line (especially a signal line over which the CCD driving signal is transmitted) coupled to the CCD 37 is diminished sufficiently. Moreover, the strength of any external noise mixed with an output signal of the CCD 37 is reduced enough to prevent deterioration of image quality.

Moreover, a luminance signal component of a video signal generated by the video signal generation circuit in the CCU 5 is input to a light adjustment signal generation circuit in the CCU 5. An average of the luminance signal components is then calculated, and a light adjustment signal indicating a deviation from a target luminance average is generated. The light adjustment signal is transmitted to an automatic iris drive circuit, which will be described later, in the TV camera 3 over the camera cable 9. Consequently, a (iris) diaphragm is driven in order to automatically control an amount of light incident on the CCD, so that the average of the luminance signal components will correspond to the target luminance average. Thus, the brightness of an object image is adjusted to a brightness level suitable for observation.

FIG. 2 shows a practical structure for the TV camera 3 serving as an endoscopic imaging apparatus of the first embodiment of the present invention.

The TV camera 3 includes a camera head 21 that withstands autoclaving so as to keep the interior thereof airtight, and a cable portion 22 which is detachably coupled to the back end of the camera head 21 and which also withstands autoclaving so as to remain watertight.

Autoclaving is a means of sterilization where an object to be sterilized is exposed to steam at a temperature ranging from 121 to 135° C. and a pressure ranging from 1.5 to 2.2 atm for 5 to 20 minutes. In the subsequent description, all references to an airtight structure or watertight structure is defined to be a structure that can maintain airtightness or watertightness during autoclaving.

The camera head 21 is, as described below, structured to basically have three layers including an outer metallic layer, an inner insulating layer inside the outer metallic layer, and an internal shielding layer isolated from the outer metallic layer by the inner insulating layer and located inside the inner insulating layer. The front end of the outer metallic layer is sealed hermetically using an optical member. At the back end of the outer metallic layer, an insulating material is used to hermetically couple the outer metallic layer to a metallic frame of a connector, which communicates with the internal shielding layer, inside a housing member that is an insulator covering the outer metallic layer.

An outermost circumferential portion of the camera head 21 ending at a position near a first connector 23 (or connector bearing) located at the back end thereof is shielded with an outer metallic sheathing 24. The metallic mount 25 to be attached to the eyepiece unit 13 of the rigid endoscope 2 is located at the front end of the outer metallic sheathing 24. The mount 25 is freely detachably attached to the eyepiece unit by means of a fixing screw 25a.

Moreover, a cover glass 26 serving as an optical member is hermetically fixed in a round opening in the center of the front end of the outer metallic sheathing 24 so that the cover glass can withstand autoclaving. An imaging optical system including the CCD 37 placed behind the cover glass inside camera head 21.

To be more specific, a rod lens 27 is located inside the cover glass 26 that is sealed hermetically. The outer circumference of the back end of the rod lens 27 is fixed by the inner circumference of the front end of a first inner insulating sheathing 28a placed inside the outer metallic sheathing 24.

The cover glass 26 is metallized by plating or the like to form a metallic layer on the outer circumference of the disk-like cover glass. The metallic layer is brazed or soldered to the outer metallic sheathing 24 and thus sealed hermetically.

Figure 3A:
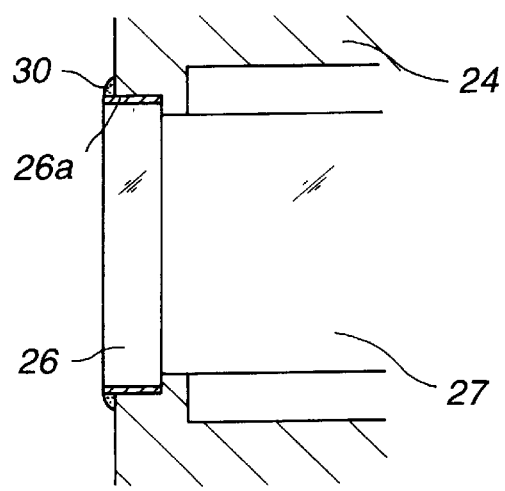
FIG. 3A is an enlarged sectional view of a portion in which the outer circumference of a cover glass is metallized to be hermetically sealed.

For example, as shown in FIG. 3A, the cover glass 26 is metallized by plating to form a metallic layer 26a on the outer circumference of the disk-like cover glass. The metallic layer 26a engaged with the round opening in the center of the front end of the outer metallic sheathing 24 is sealed hermetically by brazing 30. Thus, a hermetic seal is formed.

The back end of the first inner insulating sheathing 28a is coupled to a second inner insulating sheathing 28b placed along the inner circumference of the outer metallic sheathing 24. A first internal shielding sheathing 29a made of a metal is placed inside the first inner insulating sheathing 28a. A second internal shielding sheathing 29b located at the back end of the first internal shielding sheathing 29a is placed inside the second inner insulating sheathing 28b.

The front end of the first internal shielding sheathing 29a is engaged with the inner circumference of the front end of the first inner insulation sheathing 28a. A stator of an automatic iris unit 31 is screwed to the inner wall of the front end of the first inner insulating sheathing 28a in the vicinity of the back end of the rod lens 27.

A lens frame 32 is fixed to the back surface of the automatic iris unit 31. A system of image formation lenses 33 is locked in the lens frame 32. A filter frame 36 having a filter 35 affixed therein with a connection frame and insulation frame 34 between them is located near the back end of the lens frame 32. The filter 35 is composed of, for example, a protective cover glass, an optical low-pass filter made with a crystal filter for removing noises that cause aliasing, and an infrared cutoff filter.

An imaging device frame 38 having, for example, the CCD 37 as a solid-state imaging device affixed therein is located at the back end of the filter frame 36.

The filter frame 36 and imaging device frame 38 are mounted in a focus mechanism 39 that is located on the outer circumferential side thereof and shaped substantially annularly. A stator of the focus mechanism 39 is screwed tightly to the first internal shielding sheathing 29a.

When a driving signal is transmitted to a motor included in the focus mechanism 39, the CCD 37 is moved forward together with the filter frame 36 and imaging device frame 38 while resisting a constraining force exerted by a coil spring 41. This is illustrated in the lower part of the FIG. 2 relative to an optical axis 0. Thus, focus is achieved.

The first connector 23 located behind the CCD 37 has a connector body thereof or a connector housing metallic frame 43 thereof sheathed by an insulation frame 44 made of an insulating material to ensure watertightness. The front end of the insulation frame 44 is engaged with the outer circumference of the back end of the outer metallic sheathing 24 and screwed tightly. An O ring 45 is interposed between the insulation frame and outer metallic sheathing in order to ensure watertightness.

Moreover, the back end of the insulation frame 44 is engaged with the outer circumference of the camera cable 9. A packing 46 is mounted in the back end of the insulation frame 44 in order to realize a watertight structure. Thus, a watertight space 47 is created inside the insulation frame 44. The watertight space 47 permits entry or passage of steam from outside, but has the capability of being impervious to water from outside. An anti-breakage member 48 is mounted on the outer circumference of the back end of the insulation frame 44.

A second connector 49 having a metallic connector shielding frame 54 thereof press-fitted on a shielding sheath 55 exposed by stripping an insulation armor from the distal part of the camera cable 9 is stowed in the watertight space 47. The second connector 49 is coupled to the first connector 23 so that it can be uncoupled freely.

The camera cable 9 has a plurality of signal lines shielded by the shielding sheath 55. The plurality of signal lines extending from the distal part of the camera cable 9 is spliced to contact pins 51 jutting from behind the back end surface of the second connector 49.

The contact pins 51 are penetrated through bores in a connector body 52, and sintered by applying melted glass around the contact pins. A hermetic seal 53 is thus formed to hermetically secure the contact pins 51.

The connector body 52 is metallic and has a back end thereof brought into contact with and shielded by the metallic connector shielding frame 54. The connector shielding frame 54 communicates with the shielding sheath 55 of the camera cable 9. The shielding sheath 55 is sheathed by an insulating armor. The armor is removed from the front end of the shielding sheath 55, so that the front end can be electrically coupled to the connector shielding frame 54 via a metallic connection ring 68.

The shielding sheath 55 shields the plurality of signal lines that are incorporated therein and coupled to the CCD 37 or the like via both the connectors 23 and 49. The back end of the shielding sheath 55 is connected to a shielding-potential point in the CCU 5.

As mentioned above, the CCD 37 is stowed inside the internal shielding sheathings 29a and 29b and is isolated from the outer metallic sheathing 24 by the inner insulating sheathings 28a and 28b. The internal shielding sheathings 29a and 29b communicate with the shielding sheath 55 of the camera cable 9 via the connector frame. The back end of the shielding sheath 55 is grounded or connected to the shielding-potential point. Thus, a shielding structure capable of blocking electromagnetic waves is achieved to solve the problem concerning electromagnetic interference.

Moreover, the second connector 49 is coupled to the first connector 23. Contact pins 57 of the first connector 23 are inserted into contact pin receptors 56 located distally to the contact pins 51, whereby electrical conduction is attained.

In the first connector 23, bores are formed in a disk-shaped contact pin mounting portion of the connector housing metallic frame 43. The contact pins 57 are penetrated through the bores, and sintered by applying melted glass around them. Thus, a hermetic seal 58 is realized to secure the contact pins 57 hermetically.

Moreover, the front part of the connector housing metallic frame 43 is widened stepwise, and engaged with the outer circumference of the back end of an insulator 61 used for hermetic coupling (hereinafter a hermetic insulator). The front part of the connector housing metallic frame 43 is then secured hermetically using a binder. The outer circumference of the front end of the hermetic insulator 61 is engaged with the inner circumference of the back end of the outer metallic sheathing 24 and secured hermetically using a binder.

As shown in FIG. 2, the back end of the second internal shielding sheathing 29b is separated a bit from the hermetic insulator 61, and located inside the hermetic insulator. In this state, the back end of the second internal shielding sheathing is screwed tightly to the connector housing metallic frame 43 with a metallic locking ring 67 between them. In other words, the internal shielding layer communicates with the housing metallic frame 43 of the first connector 23. In this case, the whole circumference of the opening at the back end of the internal shielding layer is electrically coupled to that of the opening at the front end of the housing metallic frame 43 of the first connector 23 via the metallic locking ring 67. Thus, the full effect of a shield is realized.

In other words, the internal shielding layer shields the CCD 37 and its surroundings. The circumference of the opening at the back end of the internal shielding layer is electrically coupled to the housing metallic frame 43 of the first connector 23 in such a manner that no electromagnetic waves will leak out. Thus, the interior of the internal shielding layer is fully and effectively shielded from the exterior environment of TV camera 3.

Figure 3B:
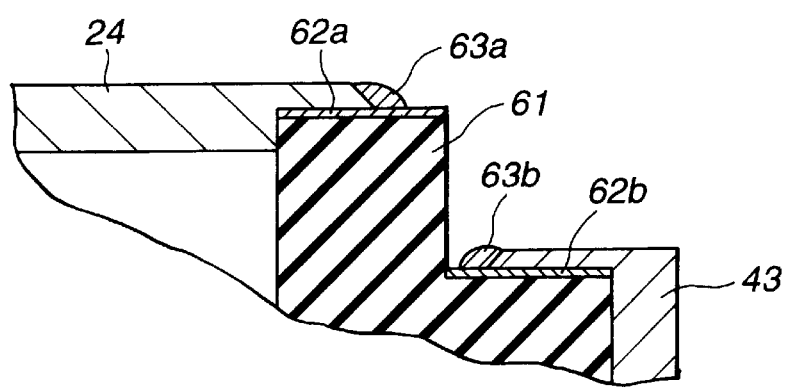

FIG. 3B shows the structure of a connection member for joining the hermetic insulator 61 and outer metallic sheathing 24 and the structure of a connection member for linking the hermetic insulator 61 and connector housing metallic frame 43 in enlargement. As shown in FIG. 3B, the outer circumference of the hermetic insulator 61 is stepped. The step portions are provided with a necessary creeping distance for the outer metallic sheathing 24 and shielding-potential point. Hermetic sealing layers 62a and 62b that are metallized by plating a metal or the like are placed on the two outer-circumferential areas that are the step portions and serve as coupling surfaces. Brazing fillers 63a and 63b serving as a hermetic binder are used to hermetically couple the interfaces between the outer-circumferential areas and the outer metallic sheathing 24 and connector housing metallic frame 43. Thus, a hermetic coupling means providing resistivity to autoclaving (sterilization under high-temperature and high-pressure steam) (resistivity to the high temperature and high-pressure steam and impermeability to the steam) is realized.

As mentioned above, the outer metallic sheathing 24 and connector housing metallic frame 43 are joined by the hermetic insulator 61. The inside of the outer metallic sheathing 24 and connector housing metallic frame 43 is defined as hermetic space 64. The linkage feature for linking the outer metallic sheathing 24 and connector housing metallic frame 43 is stepped, and the outer metallic sheathing 24 and connector housing metallic frame 43 are separated from each other. Thus, necessary isolation and resistivity are ensured.

In the thus structured embodiment, the back part of the outer metallic sheathing 24 is sheathed by the insulation frame 44. The hermetic insulator 61 is interposed between the outer metallic sheathing 24 and the connector housing metallic frame 43 of the first connector 23, which communicates with the internal shielding sheathing inside the insulation frame 44. The outer metallic sheathing 24 and connector housing metallic frame 43 are joined and fixed hermetically by the hermetic sealing layers 62a and 62b that are metallized and separated from each other by a certain distance. Thus, even when the camera head is autoclaved, steam can be prevented from invading into the hermetic space 64.

Resin sealing or the like deteriorates over time because of invasion of steam. In this embodiment, invasion of steam can be prevented reliably for a prolonged period of time so that deterioration or the like can be avoided.

Moreover, the shielding sheathings 29a and 29b are placed to be isolated from the outer metallic sheathing 24 to be coupled to the rigid endoscope 2 by means of the inner insulating sheathings 28a and 28b. The imaging device is located inside the shielding sheathings 29a and 29b. The shielding sheathings 29a and 29b are coupled to the shielding sheath of the camera cable 9 via the frame or the like of the hermetically structured first connector 23. The signal lines are shielded entirely. Thus, the strength of electromagnetic waves that are radiated to the outside of the shielding sheathings as noise can therefore be minimized. Moreover, a mixture of external noise with transmitted image signals can be fully suppressed. This results in an image of good quality. The shielding structure can solve the problems arising from electromagnetic interference.

Moreover, in this embodiment, the first connector 23 connected to the imaging device is also structured hermetically. The first connector 23 is freely detachably attached to the camera cable 9 with the second connector 49 between them. Unlike the prior art, even if steam enters through the armor of the camera cable 9 which has plasticity, the steam will not adversely affect the hermetic space 64.

Moreover, the camera cable 9 is spliced to the first connector 23 via the second connector 49 so that it can be freely separated. If part of the cable is broken, it can be repaired easily, compared with when the cable cannot be separated from the connector.

Moreover, the automatic iris mechanism or the like is stowed in the hermetic space 64. Thus, a failure deriving from steam damage can be efficiently prevented.

Incidentally, the shielding sheathing (29a or 29b) is not limited to a sheathing formed with a metallic frame. Alternatively, a conducting layer may be formed inside the inner insulating sheathings 28a and 28b by plating the inner surfaces of the inner insulating sheathings with a metal or coating them with conductive paint.

Moreover, solder or another brazing filler having a different fusing point may be substituted for the brazing fillers 63a and 63b in the first embodiment shown in FIG. 3B. For example, the hermetic sealing layer 62a to be engaged with the hermetic insulator 61 and the outer metallic sheathing 24 may be sealed by applying a brazing filler 63a that has a high fusing point. The hermetic sealing layer 62b to be engaged with the connector housing metallic frame 43 may then be sealed by applying a solder 63b whose fusing point is lower than that of the brazing filler 63a.

The foregoing method can overcome the drawback of imperfect sealing when a portion brazed with the brazing filler 63b is fused during soldering of the connector housing metallic frame 43 and hermetic sealing layer 62b using the solder 63b. In short, the sealing process can thus be simplified.

Incidentally, a brazing filler having a high fusing point may be used as the brazing filler 63b and a solder may be used instead of the brazing filler 63a.

Moreover, in the first embodiment, like the fifth embodiment that will be described later, the camera head 21 includes the outer metallic sheathing 24, first inner insulating sheathing 28a, and first internal shielding sheathing 29a as a plurality of sheathing members or sheathing layers constituting a housing member for shielding the imaging optical system that includes the CCD 37. Linkage fixtures for joining the plurality of sheathing members or sheathing layers may be gathered distally to the image plane of the CCD 37 on the side of the (eyepiece unit 13) endoscope 2. Even when the camera head is autoclaved or brought to an ambient condition of a high temperature, deterioration of the optical characteristics of the camera head can be avoided.

Figure 4:
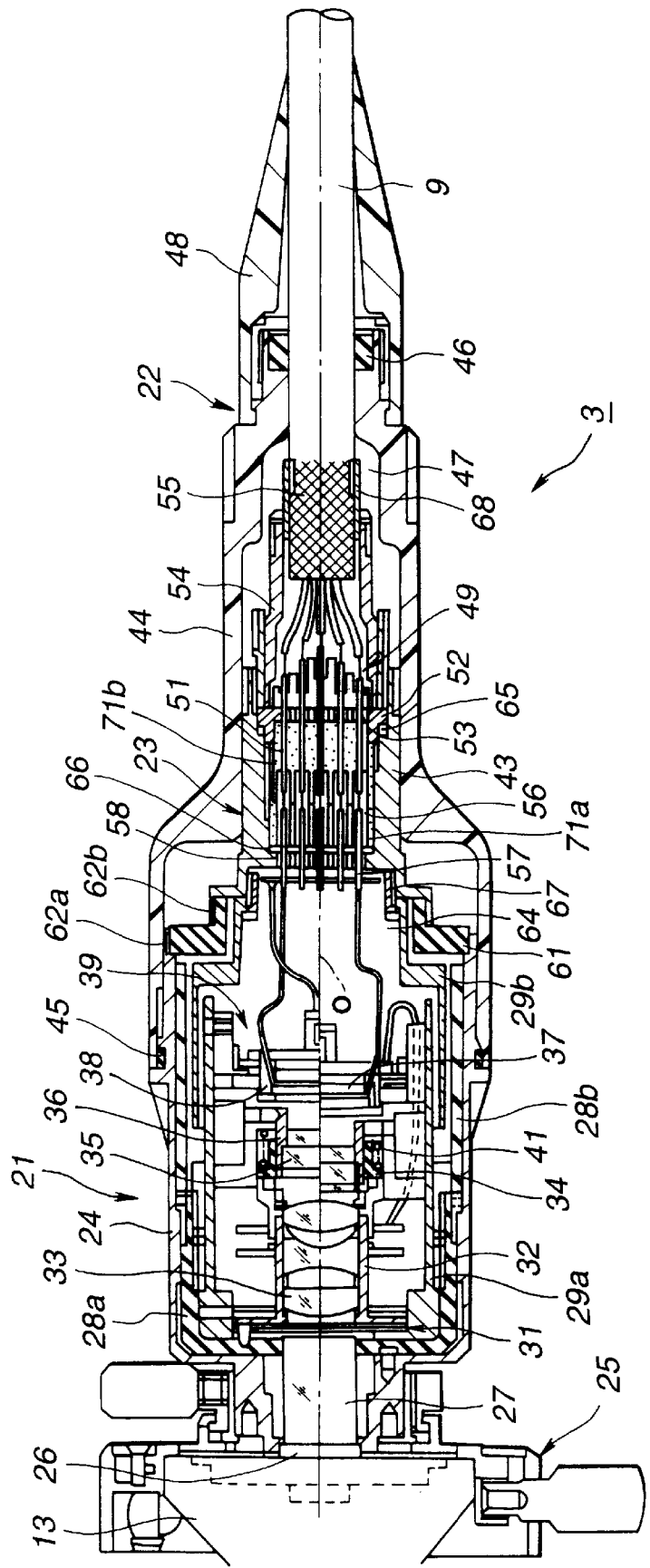
FIGS. 4 to 6 relate to a second embodiment of the present invention.
Figure 5:
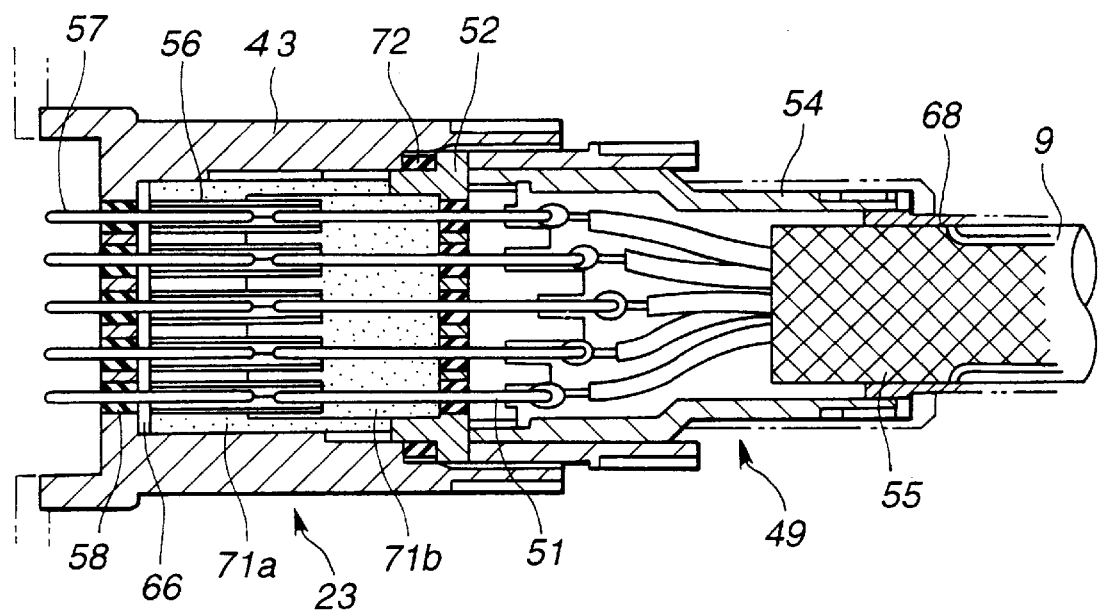

Referring to FIGS. 4 and 5, a second embodiment of the present invention will be described below.

In this embodiment, the portions of the first connector 23 and second connector 49 of the first embodiment, which are coupled to each other, are structured as described below.

As shown in FIG. 5, the contact pin receptors 56 of the second connector 49 to be coupled to the first connector 23 are sealed with a resin. Thus, a resin seal 71a is formed around the contact pin receptors 56. Additionally, the contact pins 51 toward the hermetic seal 58 are also sealed with a resin. Thus, a resin seal 71b is formed around the contact pins 51.

Moreover, a metallic sealing member 65 is sandwiched between the connector body 52 and connector housing metallic frame 43. The connector body and connector housing metallic frame are thus sealed hermetically. Consequently, steam coming from the camera cable 9 is prevented from invading into a coupling space 66 created by coupling the connectors.

The foregoing structure is adopted in order to prevent imperfect isolation deriving from moisture in the air or moisture condensed on the surfaces of the pins or the surface of the insulator. Additionally, occurrence of a short circuit between adjoining contact pins is prevented. Moreover, occurrence of imperfect contact is also prevented.

Furthermore, splicing or separating the camera cable 9 can be achieved without destruction of the hermetic space 64 in the camera head 21.

Incidentally, the metallic sealing member 65 is made of, for example, an aluminum alloy and can be replaced with a new one at the time of repair.

In the example shown in FIG. 5, a gasket member 72 is sandwiched between the connector body 52 and connector housing metallic frame 43 in place of the metallic sealing member 65 shown in FIG. 4. Aside from a metallic gasket, an elastic member (for example, a fluorocarbon rubber ring or fluorine-coated O ring) may be used as the gasket.

The other components are identical to those of the first embodiment.

This embodiment provides the same operations and advantages as the first embodiment. In addition, since the contact pins 51 of the second connector 49 are supported by a resin sealing member, the first and second connectors can be coupled to each other more reliably.

Figure 6:
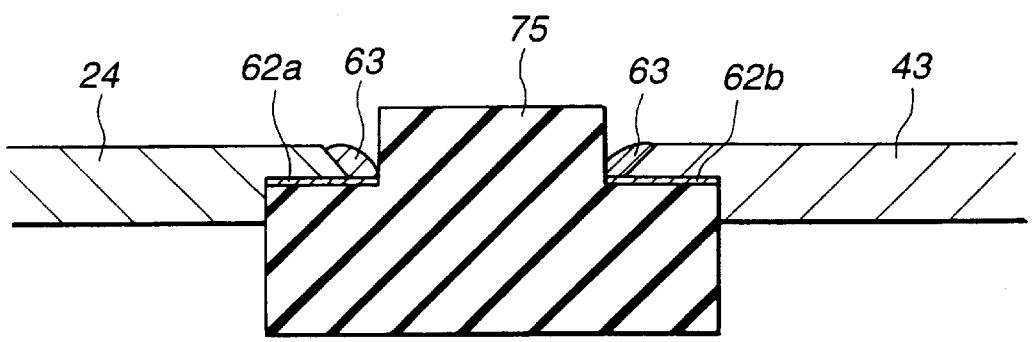

FIG. 6 shows a major portion of a variant of the second embodiment. In the first and second embodiments, the hermetic insulator 61 has a substantially L-shaped section. In this variant, a hermetic insulator 75 has a section whose center part is raised so that the center part will have a larger diameter.

Both margins of the hermetic insulator 75 are metallized to form the hermetic sealing layers 62a and 62b. The outer metallic sheathing 24 and connector housing metallic frame 43 are hermetically joined and fixed using a brazing filler 63.

In this structure, since the center part is raised, the isolation and resistivity of both the margins can be maintained more reliably. The advantages are identical to those of the first and second embodiments.

In the first and second embodiments, the first and second inner insulating sheathings 28a and 28b are used to ensure isolation between the outer metallic sheathing 24 and the first and second internal shielding sheathings 29a and 29b. An air layer may be substituted for part or the whole of the first and second inner insulating sheathings in order to ensure necessary isolation. In this case, the thickness of the air layer is set to a value equal to or larger than a value permitting necessary isolation and resistivity.

Figure 7:
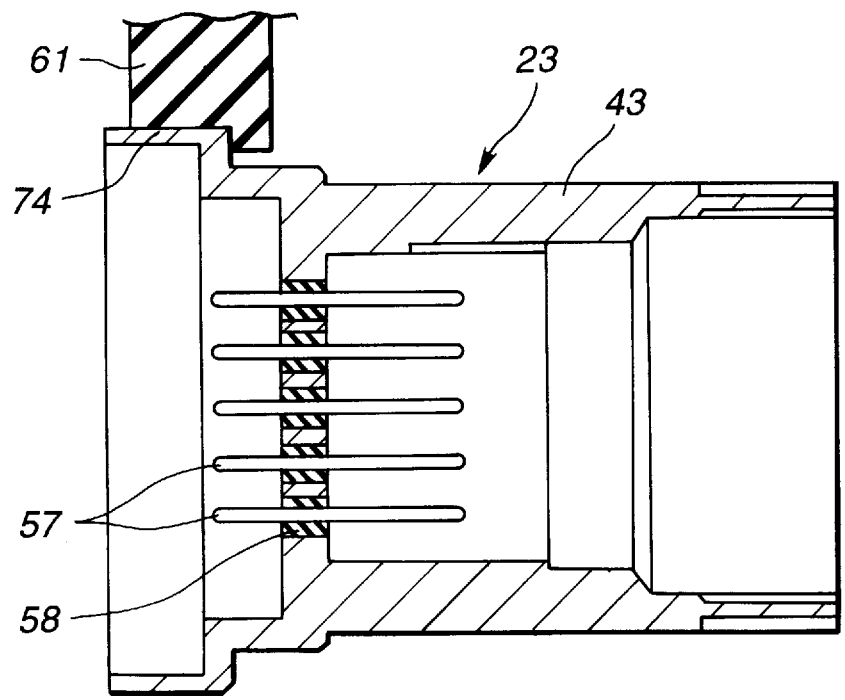
FIG. 7 is a sectional view showing a portion in which a first connector and insulator are sealed hermetically in a third embodiment of the present invention.

Next, referring to FIG. 7, a third embodiment of the present invention will be described below.

In the first embodiment, for example, the first connector 23 is fixed to the outer surface of the hermetic insulator 61 using a binder. In this embodiment, the first connector 23 is fixed to the inner surface of the hermetic insulator 61 using a binder. A portion of the first connector to be sealed and fixed to the hermetic insulator 61 is formed as a thin scaling portion 74 having a smaller thickness than the remaining portions of first connector 23. The thin sealing portion 74 is hermetically fixed to the hermetic insulator 61 using a fused brazing filler.

The other components are identical to those of the first embodiment.

According to this embodiment, the thin sealing portion 74 can be heated locally and coupled easily to the hermetic insulator using a fused solder or the like. Moreover, the fused solder may be applied to the metallized portions. The small thickness of portion 74 contributes to a smaller diameter of first connector 23.

Incidentally, when a binder is used for hermetic coupling, the hermetic insulator 61 may be fixed to the first connector by applying a solder of a high-temperature type to the inner circumference of the hermetic insulator. Thereafter, the outer circumference of the hermetic insulator 61 may be soldered to the outer metallic sheathing 24 using a low-temperature type solder whose fusing point is lower than that of the high-temperature type solder. In this case, the hermetic insulator 61 may be hermetically coupled and fixed independently to the first connector and outer metallic sheathing using a solder, so that coupling and fixing of the hermetic insulator to one of the first connector and outer metallic sheathing will not affect coupling and fixing thereof to the other.

Figure 8:
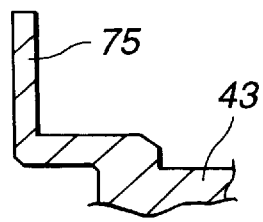
FIG. 8 is a sectional view showing a thin scaling part in the variant shown in FIG. 7.

Like a variant shown in FIG. 8, the thin sealing portion 75 may be shaped like a flange. In this case, a binder layer made of a fused brazing filler can be controlled easily. The other components are identical to those of the third embodiment.

Figure 9:
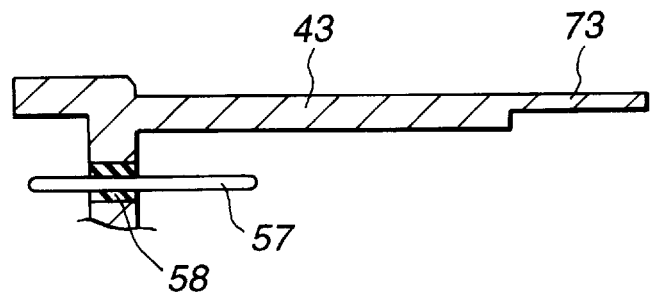
FIG. 9 is a sectional view showing a thin sealing part in the variant shown in FIG. 7.

Moreover, a thin sealing portion 73 may be, as shown in FIG. 9, a portion located far away from a glass hermetic seal. In this case, when the connector housing metallic frame 43 is fixed to the hermetic insulator using a fused binder, the glass hermetic seal will be minimally affected in an adverse manner by heat.

Figure 10:
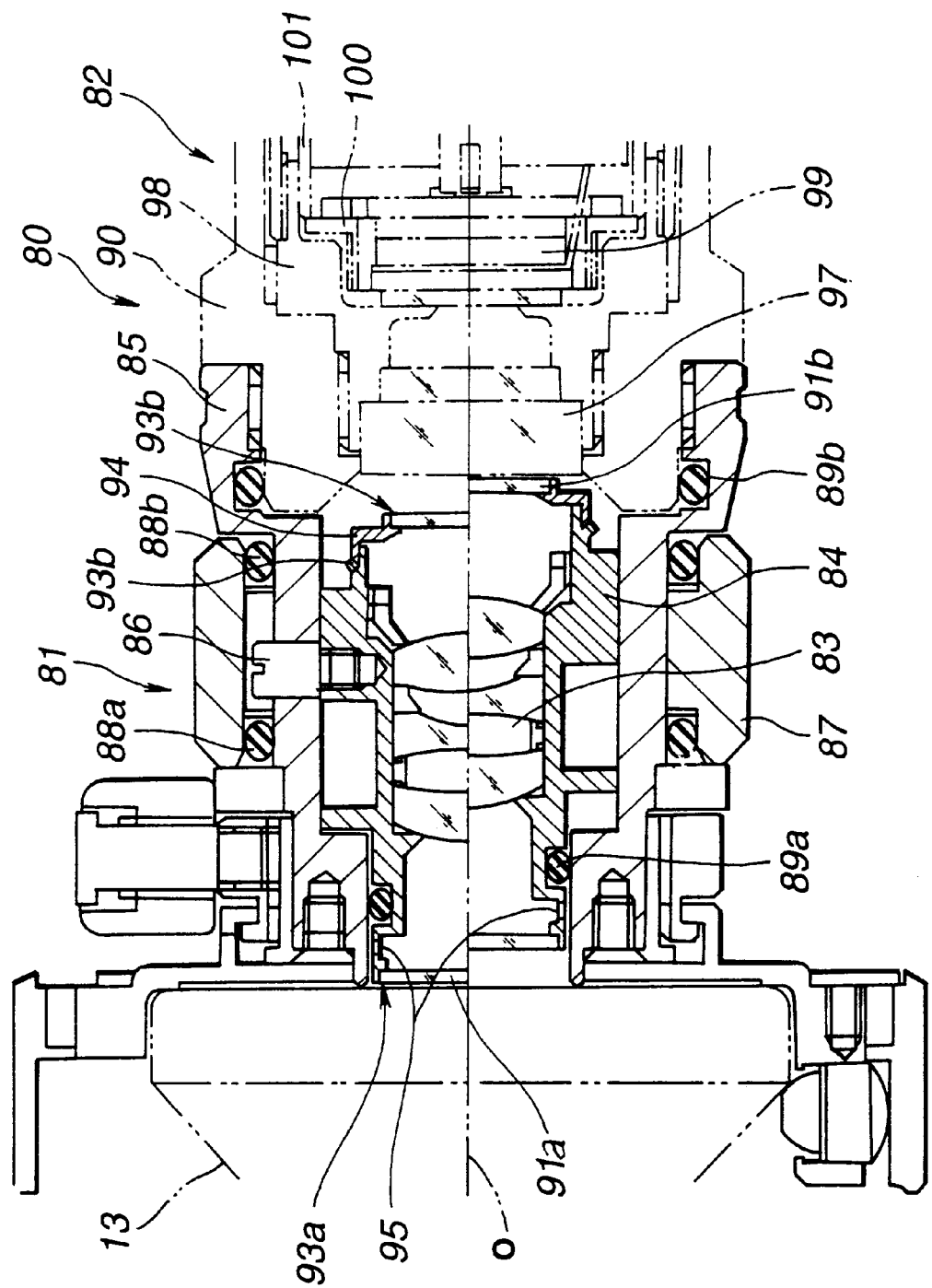

Next, referring to FIG. 10, a fourth embodiment of the present invention will be described below.

In an endoscopic imaging apparatus 80 of this embodiment, the camera head 21 of the first embodiment is divided into an optical adapter 81 and camera head 82.

The optical adapter 81 has a metallic lens frame 84, in which a system of image formation lenses 83 is locked, placed in a cylindrical locking frame 85 so that the metallic lens frame 84 can slide freely. A pin 86 projects out of the lens frame 84. The pin 86 penetrates through a spiral groove formed in the locking frame 85, and is fitted in an elongated groove in a focus ring 87 that is freely rotatable and located outside the locking frame 85.

By turning the focus ring 87, the lens frame 84 is moved together with the pin 86 in the direction of the optical axis. Thus, focusing of an image can be achieved.

O rings 88a and 88b are placed at front-end and back-end positions on the inner circumference of the focus ring 87, whereby watertightness is ensured.

Moreover, an O ring 89a is placed at a position near the front end of the lens frame 84 on the outer circumference of the lens frame 84. Thus, watertightness is ensured.

A screw portion of a housing member 90 outlining the camera head 82 is engaged with a screw portion at the back end of the locking frame 85. An O ring 89b is interposed between the locking frame 85 and housing member 90 in order to ensure watertightness.

Figure 11A:
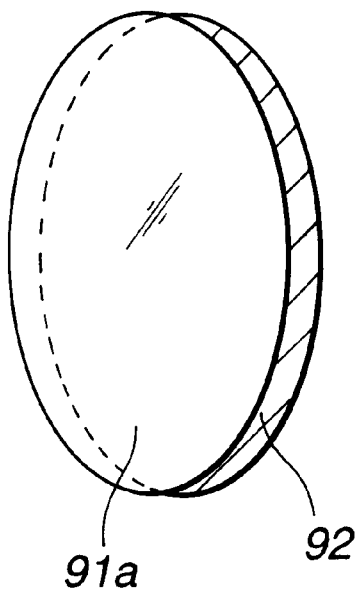
FIGS. 11A and 11B are perspective views showing a cover glass having a metallic film coated thereon.

Moreover, the lens frame 84 in the optical adapter 81 is structured hermetically as described below. That is to say, an opening at the front end of the lens frame 84 is hermetically sealed by a cover glass 91a. The cover glass 91a is, as shown in FIG. 11A, metallized with a metallic film 92 formed by plating the lateral circumferential surface thereof. The cover glass 91a is fitted into the opening at the front end of the lens frame 84, and hermetically sealed with a fused solder or brazing filler. Thus, a hermetic seal 93a is formed.

Figure 11B:
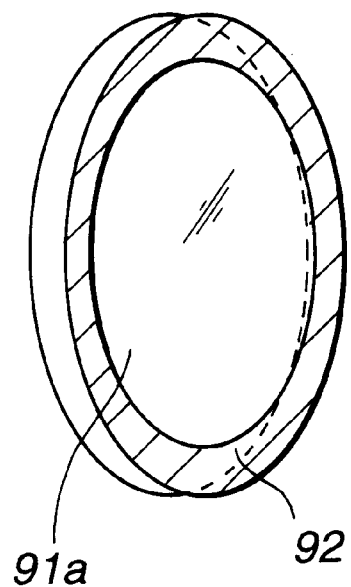

Alternatively, the cover glass 91 a may be, as shown in FIG. 11B, metallized by coating the annular margin thereof, which abuts on a locking jut of the lens frame 84, with a metallic film 92.

Moreover, a metallic sealing ring 94 has a hermetic seal 93b for hermetically sealing the back end of the lens frame 84 with a cover glass 91b that is metallized with a metallic film 92 like the cover glass 91a. The metallic sealing ring 94 is engaged with the outer circumference of the back end of the lens frame 84. The hermetic seal 93b is realized by applying a solder or brazing filler to the interface between the sealing ring 94 and the back end of the lens frame 94. Alternatively, the sealing ring 94 may be omitted and the cover glass 91b is instead hermetically affixed directly in the opening at the back end of the lens frame 84.

Figure 12:
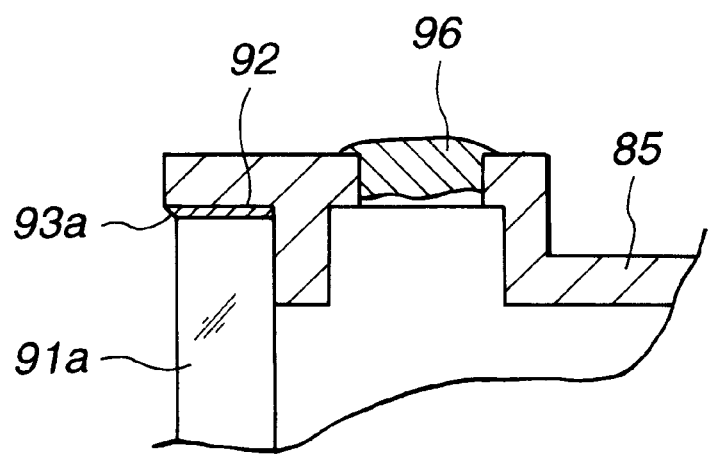

Moreover, a bore 95 for deaeration is formed near, for example, the front end of the lens frame 84. Expanded air in the lens frame 84 is evacuated through the bore 95 at the time the lens frame 84 is hermetically sealed. After the completion of hermetic sealing, as shown in FIG. 12, the bore 95 is sealed with a sealing material 96 such as a solder or brazing filler or an inorganic binder.

Moreover, a filter frame 98 in which a filter 97 is fixed hermetically and which is made of an insulating material is screwed inside the housing metallic member 90 of the camera head 82. A metallic device frame 100 having a CCD 99 incorporated therein is placed behind the filter 97.

The device frame 100 is coupled to a shielding frame 101 extending backward therefrom. Moreover, the filter frame 98 is coupled to an insulation frame extending backward therefrom. The insulation frame isolates the shielding frame 101 from the housing metallic member 90.

The back portion of the camera head 82 has substantially the same structure as that of, for example, the first embodiment.

According to this embodiment, the outer circumference of the cover glass 91a or the like or the margin of the surface of the cover glass 91a is metallized. The cover glass 91a is affixed in the metallic lens frame 84 and sealed hermetically using a binder such as a brazing filler. In this manner, hermetic sealing can be achieved more successfully than if is performed using an adhesive. Moreover, the bore 95 is formed in order to evacuate the expanded air from the inside of the lens frame at the time of hermetic sealing. After the hermetic sealing is completed, the bore 95 is sealed with a sealing material 96 such as a brazing filler. Therefore, the task of sealing is not rendered difficult due to a high internal pressure, and assembly can be achieved easily.

Moreover, the cover glass 91a or the like has the outer circumference thereof or the margin of the surface thereof metallized. When the temperature gets high during autoclaving, heat is applied to the cover glass in the circumferential direction thereof. Compared with when heat is applied locally, higher resistivity to thermal expansion can be attained. Thus, the cover glass becomes harder to break in the present invention.

The other advantages are substantially identical to those of the first embodiment.

Alternatively, the cover glass 91a may be omitted, whereupon the first lens included in the system of image formation lenses 83 or any other optical lens or optical filter may be sealed hermetically.

The sealing means or method described in relation to the optical adapter 81 can be adapted to the camera head 82 or the like.

A ceramic or heatproof engineering plastic, for example, may be used to form the hermetic insulator 61 or the like.

The plastic may be a super engineering plastic such as PEEK or PPS.

Also, the glass hermetic seals 53 and 58 may be made of a ceramic or resin (super engineering plastic) other than glass.

The hermetic sealing layers 62a and 62b may be metallic layers with a nickel or cobalt base, or with a gold or molybdenum-manganese alloy base.

The binder may be a brazing filler with a gold or silver base, a solder with a tin-palladium alloy base, a low-fusing point glass, or an inorganic binder.

A ceramic may be used to make the hermetic insulator 61 and a ceramic solder or low-fusing point glass may be used to hermetically seal the hermetic insulator 61, the outer metallic sheathing 24, and the connector housing metallic frame 43 together. Coordination of materials in this manner leads to reduced manufacturing costs.

In the example described as the first embodiment, the camera head 21, which has incorporated therein the imaging optical system with the solid-state imaging device, is structured to have three layers comprised of the outer metallic layer, the insulating layer, and the shielding layer. At least the solid-state imaging device is incorporated inside the shielding layer and sealed hermetically. The present invention, however, is not limited to this structure. The described embodiment can be readily adapted for use as a camera head unit that is attached to an endoscope directly or via an adapter or the like, and can include a solid-state imaging device, an electric diaphragm driving mechanism, focus driving mechanism, or power variation driving mechanism incorporated therein, and can include an optical system or be attached to an optical adapter unit.

Moreover, embodiments constructed by combining parts of the aforesaid embodiments are within the scope of the present invention.

According to the aforesaid first through fourth embodiments, there is provided an endoscopic imaging apparatus which is attached to an endoscope directly or via an adapter, and in which an imaging optical system including at least a solid-state imaging device is sealed hermetically.

The endoscopic imaging apparatus includes an outer metallic sheathing that forms a hermetic sealing member in cooperation with an optical member, an inner shielding sheathing for shielding the solid-state imaging device, and an internal insulating layer interposed between the outer metallic sheathing and internal shielding sheathing.

A hermetic coupling means is included for hermetically coupling the internal shielding sheathing to a frame of a hermetic connector that is spliced to a shielding sheath of a cable while conductivity is maintained. The hermetic coupling means is also used to hermetically couple the outer metallic sheathing to the internal shielding sheathing with an insulating material between them. The solid-state imaging device is shielded with a shielding means. The problem arising from electromagnetic interference can therefore be solved. Additionally, the insulating material and a metal element are hermetically sealed together. Consequently, the endoscopic imaging apparatus can be autoclaved.

Next, an endoscopic imaging apparatus of a fifth embodiment which is structured so that the optical performance will not deteriorate despite a change in ambient temperature during autoclaving or the like will be described below.

Prior to a description of the most preferred variant of the fifth embodiment, various alternative variants will be described beginning with the first variant with reference to FIGS. 13 and 14. In the subsequent variants and embodiments, the same reference numerals will be assigned to the same components.

Figure 13:
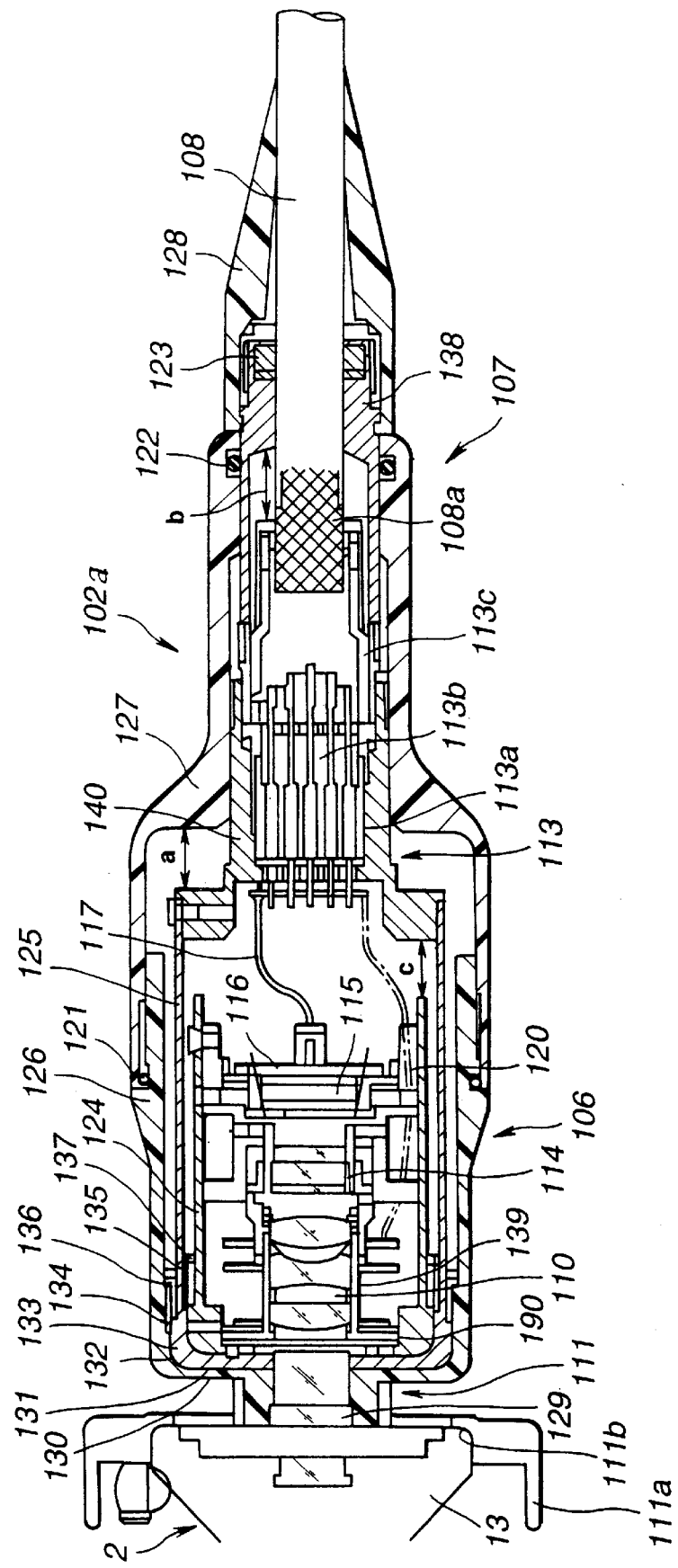
FIGS. 13 and 14 relate to a first variant of a fifth embodiment of the present invention.

FIG. 13 shows a camera head 102a of the first variant.

The camera head 102a comprises an imaging unit 106 and a cable unit 107. A cable 108 extends from the proximal end of the cable unit 107. The proximal end of the cable 108 is provided with an electrical connector 10 that is detachably coupled to the CCU 5 shown in FIG. 1.

The distal part of the imaging unit 106 is freely detachably attached to the eyepiece unit 13 of a fiber scope or the rigid endoscope 2 by means of a mount member 111a of an optical adapter 111. In this case, the mount member 111a is coupled to the eyepiece unit 13 with a bumping surface 111b thereof abutting the end surface of the eyepiece unit 13.

The imaging unit 106 has a cover glass 129 mounted in an incident end surface thereof. Moreover, an imaging optical system composed of an image formation optical system 110, filter unit 114, and imaging device 115 is incorporated in the imaging unit. Rays traveling from the endoscope 2 through the cover glass 129 pass through the image formation optical system 110 and filter unit 114. An image is then formed on the image plane 115a (See FIG. 14) of the imaging device 115. In FIG. 13, an iris unit 190 is interposed between the cover glass 129 and image formation optical system 110. The iris unit 190, however, may be omitted.

Moreover, the imaging device 115 is connected to the CCU 5 via a peripheral circuit board 116 incorporated in the camera head 102a over an intra-head signal cable 117, intra-head connector 113 and cable 108. The intra-head connector 113 includes a plug 113a located proximally to the imaging unit 106, a receptacle 113b located distally to the cable unit 107 and spliced to the plug 113 so that it can be separated freely, and a connector cover 113c. The intra-head connector 113 is structured to be waterproof.

The imaging optical system composed of the image formation optical system 110, filter unit 114, and imaging device 115 is supported within a cylindrical lens bearing member 124 via a cylindrical lens frame 139 or CCD frame 120. Moreover, a cylindrical internal shielding sheathing 125 is placed outside the lens bearing member 124 to shield the lens bearing member 124. A cylindrical first insulation cover 126, and a cylindrical second insulation cover 127 coupled to the first insulation cover 126 are placed outside the internal shielding sheathing 125 to shield the internal shielding sheathing 125. An elastic watertight member 121 is interposed between the first insulation cover 126 and second insulation cover 127. The cover glass 129 and first insulation cover 126 are bonded to each other in a watertight fashion.

The internal shielding sheathing 125 is mechanically and electrically coupled to the intra-head connector 113. Specifically, the internal shielding sheathing 125 is fastened with a screw into a housing 140 of the plug 113a and receptacle 113b and thus electrically coupled to the intra-head connector 113.

Moreover, the housing 140 is electrically coupled to a cable shield 108a of the cable 108, which is exposed at the distal part thereof, via a connector cover 113c. Moreover, the intra-head connector 113 is coupled to a cable sealing frame 138 for bearing one end of the cable 108.

An elastic watertight member 123 is interposed between the cable sealing frame 138 and cable 108. An anti-breakage member 128 made of an elastic material is fixed to the cable sealing frame 138 so that the anti-breakage member 128 can shield the cable sealing frame 138 and cable 108 from the outside. An elastic watertight member 122 is interposed between the cable sealing frame 138 and second insulation cover 127.

In the thus structured camera head 102a, the internal shielding sheathing 125, the housing 140 and connector cover 113 of the intra-head connector 113, and the cable shield 108a constitute a shielding layer covering the various electrical devices incorporated in the camera head 102. The shielding layer contributes to stable ground and is effective in coping with electromagnetic interference.

Moreover, the first insulation cover 126 and second insulation cover 127 constitute an insulating layer, and isolate the internal circuit from the outside so as to ensure electrical safety for a user. A watertight seal between the insulation covers is ensured by providing elastic watertight members 121, 122, and 123 therebetween. Further, the first insulation cover 126 and cover glass 129 are mutually bonded in a watertight fashion, and the intra-head connector 113 is structured to be waterproof. The internal space of the camera head 102a can therefore be kept watertight.

Figure 14:
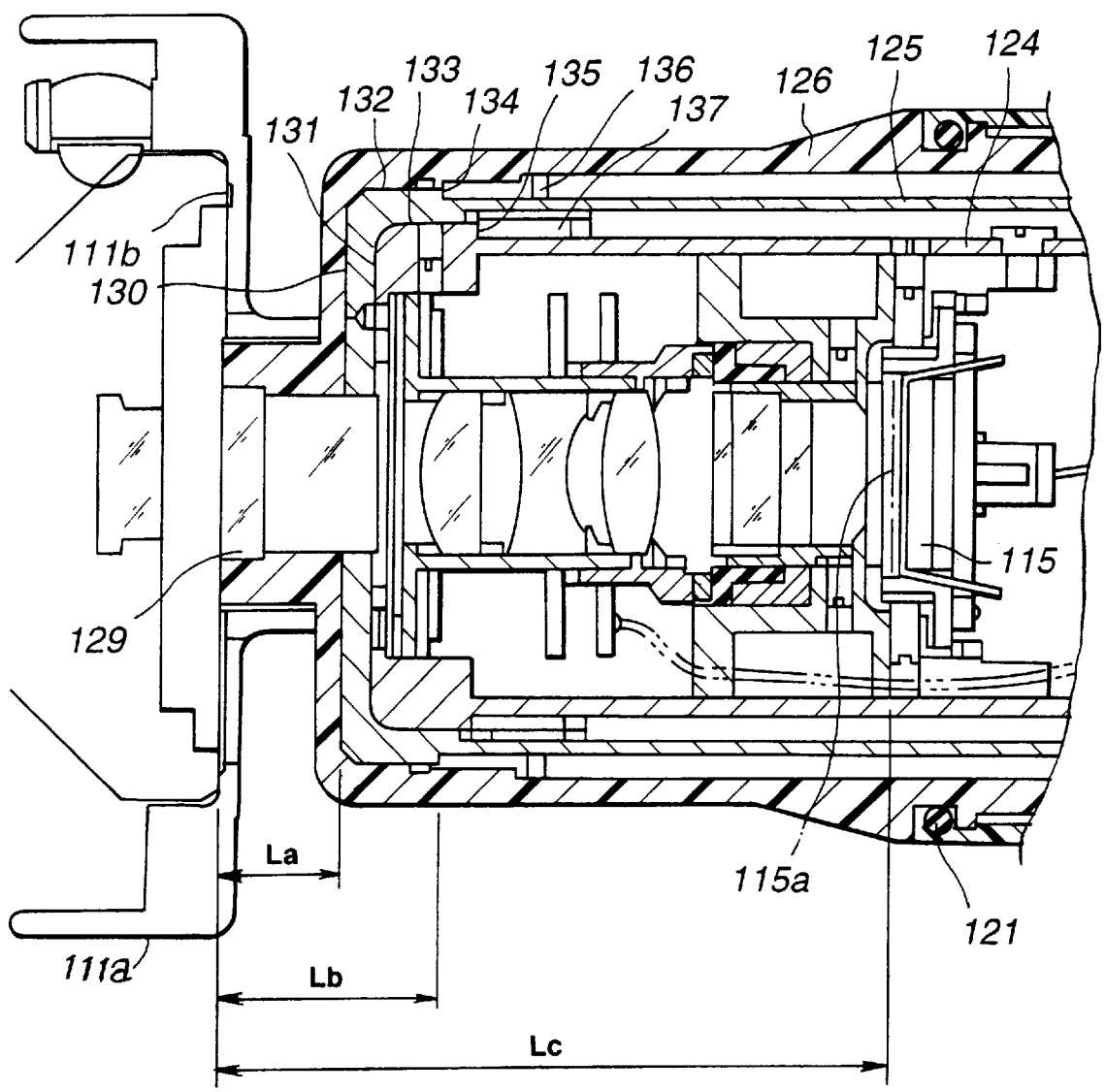

As shown in enlargement in FIG. 14, the first insulation cover 126 and internal shielding sheathing 125 are joined and fixed by a fixing member 136 while abutting against a bumping member 130.

For positioning and fixing the first insulation cover 126 and internal shielding sheathing 125 in the axial direction, an abutment end surface (connection fixture) 134 of the fixing member 136 is abutted on the internal shielding sheathing 125.

For positioning and fixing the first insulation cover 126 and internal shielding sheathing 125 in the radial direction, the outer circumference of the internal shielding sheathing 125 and the internal circumference of the first insulation cover 126 are engaged with each other by an engagement member 132. Moreover, a distance La in the optical-axis direction between the bumping surface 111b of the mount member 111a and the bumping member 130 is set to one half or smaller of a distance Lc in the optical-axis direction between the bumping surface 111b and the image plane 115a of the imaging device 115.

Moreover, a distance Lb (>La) in the optical-axis direction between the abutment end surface (connection fixture) 134 of the fixing member 136 and the bumping surface 111b) is set to one half or smaller of the distance Lc.

Moreover, the lens bearing member 124 and internal shielding sheathing 125 are coupled and fixed to each other by a fixing member 137 while being abutted against the bumping member 131. In this case, for positioning and fixing the lens bearing member 124 and internal shielding sheathing 125 in the axial direction, the abutment end surface (connection fixture) 135 of the fixing member 137 is abutted on the lens bearing member 124. For positioning and fixing the lens bearing member 124 and internal shielding sheathing 125 in the radial direction, the inner circumference of the internal shielding sheathing 125 and the outer circumference of the lens bearing member 124 are engaged with each other by the engagement member 133.

Moreover, the distance in the optical-axis direction between the bumping surface 111b of the mount member 111a and the bumping member 131 is set to one half or smaller of the distance Lc in the optical-axis direction between the bumping surface 111b and the image plane 115a of the imaging device 115.

Moreover, the distance in the optical-axis direction between the abutment end surface (connection fixture) 135 of the fixing member 137 and the bumping surface 111b (which is larger than the distance in the optical-axis direction between the bumping surface 111b and bumping member 131) is set to one half or smaller of the distance Lc.

Moreover, the distal part of the insulating layer composed of the first insulation cover 126 and second insulation cover 127, and the distal part of the shielding layer composed of the internal shielding sheathing 125, housing 140, and connector cover 113c are fixed to each other on the (bumping member 130) side of the eyepiece unit 13 of the rigid endoscope 2. The proximal parts of the insulating layer and shielding layer are permitted to independently contract or stretch in the optical-axis direction without any resistance (without interference from each other).

In other words, according to this variant, as shown in FIG. 13, the proximal part of the internal shielding sheathing 125 is separated from the end of the stepped portion of the second insulation cover 127 by a given distance "a". One of the internal shielding sheathing 125 and the covers 126 and 127 is permitted to contract or stretch without being hindered by the others.

Likewise, the proximal end of the connector cover 113c is separated from the end of the stepped portion of the cable sealing frame 138 by a given direction "b" in the optical-axis direction. The connector cover 113c is permitted to move in the optical-axis direction along with the stretch or contraction of the shielding layer, which is composed of the internal shielding sheathing 125, housing 140, and connector cover 113c, without being hindered by the cable sealing frame 138.

The proximal end of the lens bearing member 124 coupled and fixed to the internal shielding sheathing 125 on the (bumping member 131) side of the eyepiece unit 13 is separated from the distal end of the housing 140 of the intra-head connector 113 by a given distance "c".

Incidentally, all the components of the camera head 102 are made of materials resistive to a temperature at which autoclaving is carried out, or at least 135° C.

Next, the operations and advantages of the camera head 102a having the foregoing components will be described below.

To begin with, each of the connection fixture for joining the insulation covers 126 and 127; the internal shielding sheathing 125; and the connection fixture for joining the housing 140, connector cover 113c, and lens bearing member 124 are arranged on one side of the eyepiece unit 13 of the endoscope 2. Moreover, the proximal parts (on the side of the cable 8) of these components are permitted to individually contract or stretch in the optical-axis direction without any resistance.

Under a high-temperature environment, such as during autoclaving or under an environment in which the camera head is exposed to steam, or during transportation while the camera head is brought to a very low temperature, the layers may expand or contract due to heat or cold, respectively. This causes the overall lengths of the layers to change. Otherwise, the layers having different coefficients of thermal expansion may expand by different magnitudes. The changes in overall length (magnitudes of stretch based on expansion) among the layers or the differences in magnitude of expansion among the layers occur on the proximal side of the camera head. The changes and differences in magnitude of expansion must therefore be resolved on the proximal side of the camera head. Due to the presence of the insulation covers 126 and 127, internal shielding sheathing 125, and intra-head connector 113, the lens bearing member 124 becomes fully adiabatic. Thus, the overall length of the lens bearing member 124 is prevented from changing due to heat. Furthermore, changes in relative positions between the image formation optical system 110, filter unit 114, and imaging device 115 which constitute the imaging optical system are prevented from occurring to such an extent that the changes in position will impair the optical performances thereof. Moreover, the changes in positions will hardly affect the dimensions of the imaging optical system.

In other words, the changes in overall length of the layers are absorbed to suppress occurrence of stress. Moreover, deterioration of the optical performance of the imaging optical system is prevented to the greatest extent possible. The focal length and various aberrations are retained at desired levels. In other words, the different coefficients of thermal expansion of the layers will hardly affect the optical performance. The precision in the optical-axis direction of the imaging optical system will not be affected adversely by heat, since the different coefficients of thermal expansion will not bring about breakdown or deteriorate optical performance.

Moreover, the watertightness of the camera head 102a is ensured by the elastic watertight members 121, 122, and 123 that can freely contract or stretch in the optical-axis direction. The watertightness will therefore not be affected by heat.

Figure 15:
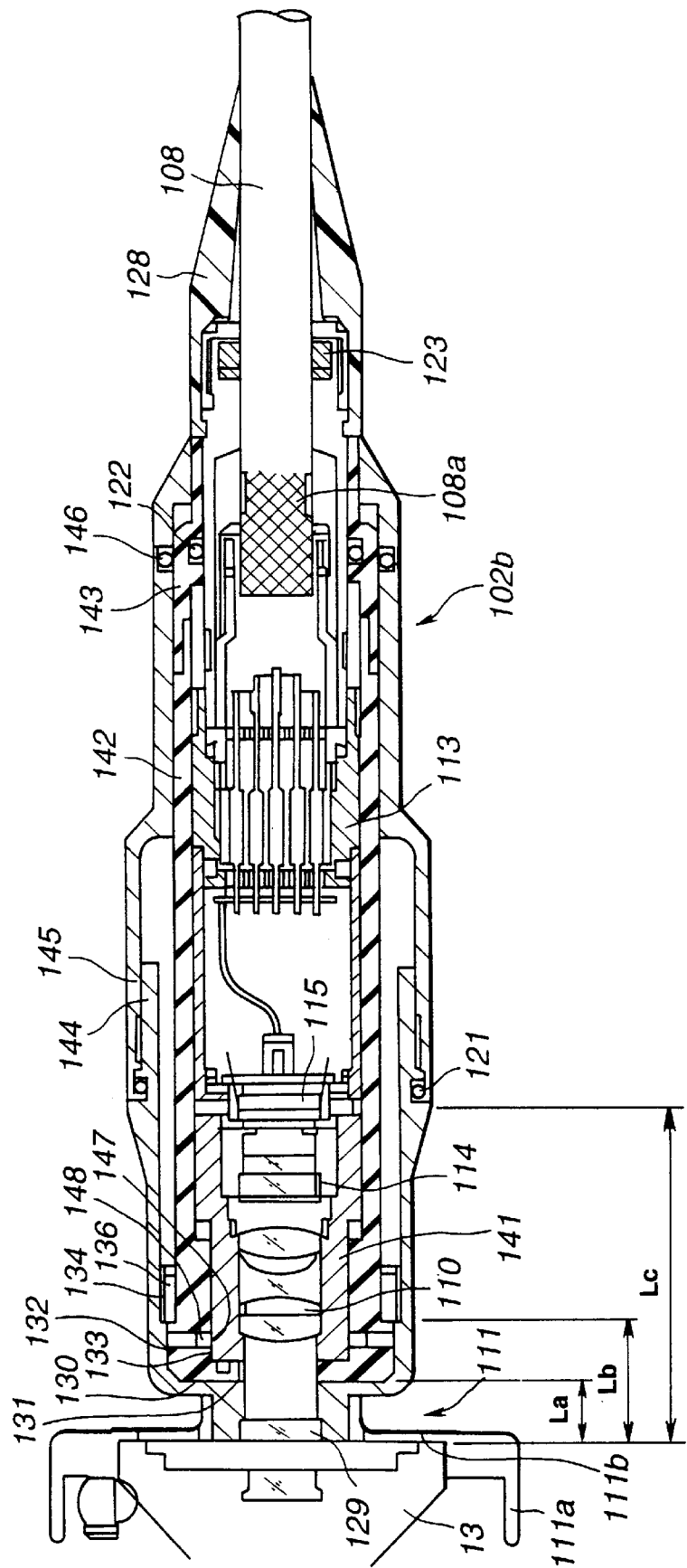
FIG. 15 is a sectional view of a camera head of a second variant of the fifth embodiment.

FIG. 15 shows a camera head 102b of a second variant of the fifth embodiment. The basic structure of the camera head 102b is identical to that of the first variant shown in FIG. 13. Only the differences from the first variant will be described below.

In the camera head 102, the imaging optical system composed of the image formation optical system 110, filter unit 114, and imaging device 115 is shielded and supported by an optical bearing/shielding sheathing 141. The optical bearing/shielding sheathing 141 is structurally and electrically coupled to an intra-head connector 113.

A first insulation cover 142 and second insulation cover 143 are placed outside the optical bearing/shielding sheathing 141 and intra-head connector 113. A first housing metallic cover 144 and second housing metallic cover 145 are placed outside the insulation covers.

Moreover, an elastic watertight member 146 is interposed between the second housing metallic cover 145 and second insulation cover 143. An elastic watertight member 121 is interposed between the first housing metallic cover 144 and second housing metallic cover 145. The cover glass 129 is bonded to the first housing metallic cover 144 in a watertight fashion.

Moreover, the first insulation cover 142 and housing metallic cover 144 are joined and fixed by the fixing member 136 while being abutted against the bumping member 130. For positioning and fixing the first insulation cover 142 and housing metallic cover 144 in the axial direction, the abutment end surface (connection fixture) 134 of the locking member 136 is abutted on the first insulation cover 142. For positioning and fixing the first insulation cover 142 and housing metallic cover 144 in the radial direction, the outer circumference of the first insulation cover 142 and the inner circumference of the housing metallic cover 144 are engaged with each other by the engagement member 132. Moreover, the distance La in the optical-axis direction between the bumping surface 111b of the mount member 111a abutting the end surface of the eyepiece unit 13 and the bumping member 130 is set to one half or smaller of the distance Lc in the optical-axis direction between the bumping surface 111b and the image plane 115a of the imaging device 115. Moreover, the distance Lb (>La) in the optical-axis direction between the abutment end surface (connection fixture) 134 of the fixing member 136 and the bumping surface 111b is set to one half or smaller of the distance Lc.

Moreover, the optical bearing/shielding sheathing 141 and first insulation cover 142 are joined and fixed by a connection/fixation screw 148 having a conical tip (not shown). For positioning and fixing the optical bearing/shielding sheathing 141 and first insulation cover 142 in the axial direction, the connection/fixation screw 148 is inserted into a connection fixture 147. For positioning and fixing the optical bearing/shielding sheathing 141 and first insulation cover 142 in the radial direction, the inner circumference of the first insulation cover 142 and the outer circumference of the optical bearing/shielding sheathing 141 are engaged with each other by the engagement member 133.

Moreover, the distance in the optical-axis direction between the bumping surface 111b of the mount member 111a and the bumping member 131 is set to one half or smaller of the distance Lc in the optical-axis direction between the bumping surface 111b and the image plane 115a of the imaging device 115. Moreover, the distance in the optical-axis direction between the connection fixture 147 to be mated with the connection/fixation screw 148 and the bumping surface 111b (which is larger than the distance in the optical-axis direction between the bumping surface 111b and the bumping member 131) is set to one half or smaller of the distance Lc.

Moreover, the distal parts of the insulation covers 142 and 143, shielding sheathing 141, and intra-head connector 113 are fixed to one another on the (bumping member 130) side of the eyepiece unit 13 of the endoscope 2. The proximal parts thereof (on the side of the cable 108) are permitted to individually contract or stretch in the optical-axis direction without any resistance.

In this variant, the iris unit 190 may be interposed between the cover glass 129 and optical bearing/shielding sheathing 141. Moreover, the connection/fixation screw 148 may be structured like the connection member 136.

The camera head 102b having the foregoing components can provide the same operations and advantages as those of the first variant. Moreover, the insulation covers 142 and 143 are protected by the housing metallic covers 144 and 145. Thus, the strength of the whole camera head is improved. Furthermore, the screw 148 having a conical tip (not shown) is mated to the connection fixture 147, which easily secures optical bearing/shielding sheathing 141 to insulation cover 142. This results in improved assembling efficiency.

Figure 16:
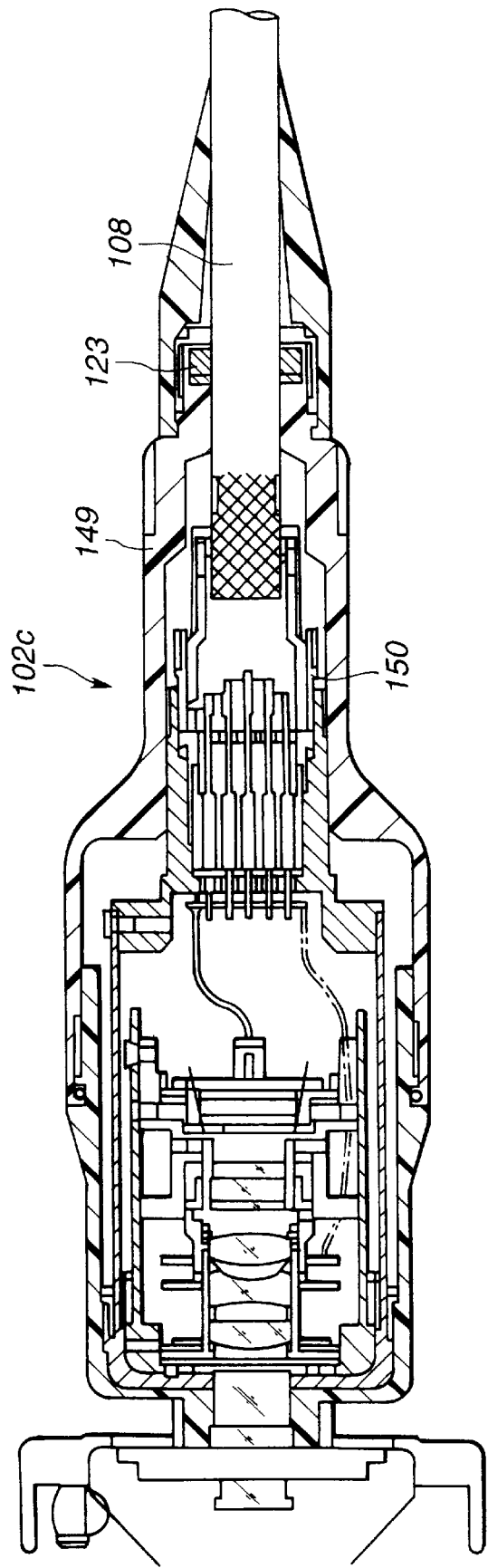
FIG. 16 is a sectional view of a camera head of a third variant of the fifth embodiment.

FIG. 16 shows a camera head 102c of a third variant of the fifth embodiment. The basic structure of the camera head 102c is identical to that of the first variant. Only the differences from the first variant will be described below.

In the camera head 102c, the second insulation cover 127 and cable sealing frame 138 of the first variant shown in FIG. 13 have been united with each other to form an insulation cover 149. An elastic watertight member 123 is interposed between the insulation cover 149 and cable 108. The intra-head connector 113 is provided with a connector presser 150 for immobilizing the plug 113a and receptacle 113b. The other components are identical to those of the first variant.

According to the foregoing structure, the same operations and advantages as those of the first variant are provided. Moreover, the second insulation cover 127 and cable sealing frame 138 of the first variant have been united with each other. Thus, parts such as the elastic watertight member 122 (See FIG. 3) and cable sealing frame 138 can be omitted.

Figure 17:
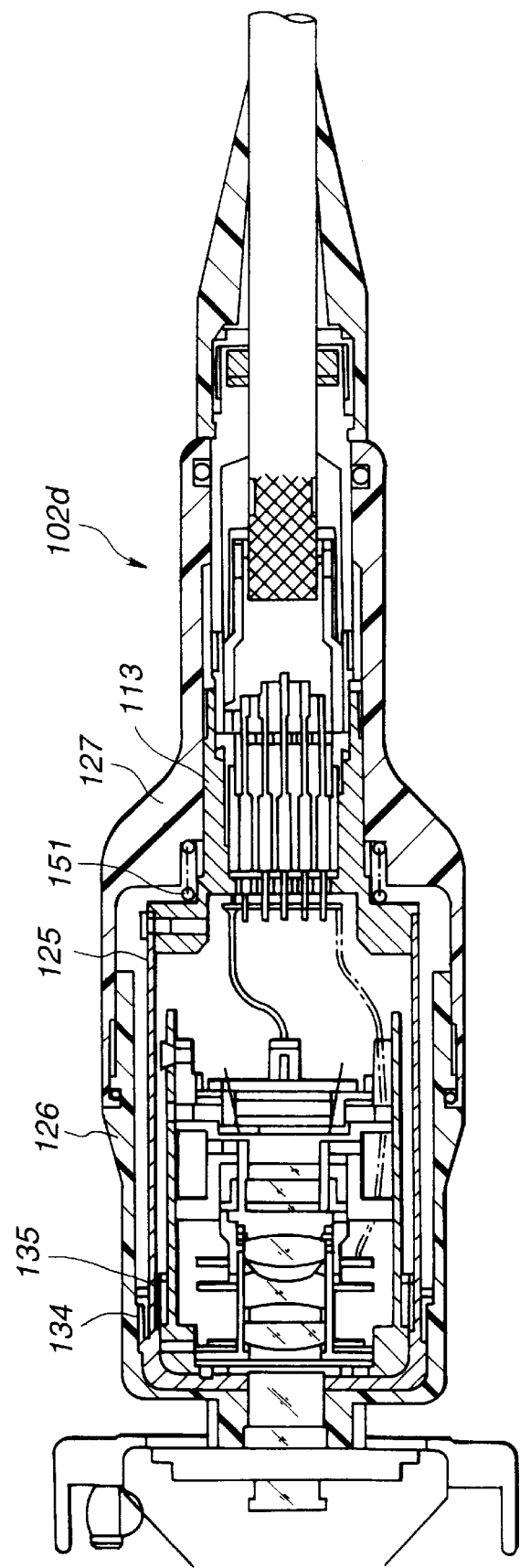
FIG. 17 is a sectional view of a camera head of a fourth variant of the fifth embodiment.

FIG. 17 shows a camera head 102d of a fourth variant of the fifth embodiment. The basic structure of the camera head 102d is identical to that of the first variant. Only the differences from the first variant will be described below.

In the camera head 102d, an elastic constraining member 151 such as a coil spring is located proximally to the connection fixtures 134 and 135, or more particularly, interposed between the intra-head connector 113 and second insulation cover 127. The elastic constraining member 151 may be interposed between the internal shielding sheathing 125 and second insulation cover 127. The other components are identical to those of the first variant.

According to the foregoing structure, the same operations and advantages as those of the first variant are provided. Moreover, the elastic constraining member 151 changes its length according to a change in overall length of the insulating layer composed of the insulation covers 126 and 127, the shielding layer formed by the internal shielding sheathing 125, or the intra-head connector 113 deriving from thermal expansion. A certain constraining force is therefore imposed on the intra-head connector 113 and second insulation cover 127. This results in improved optical precision.

Figure 18:
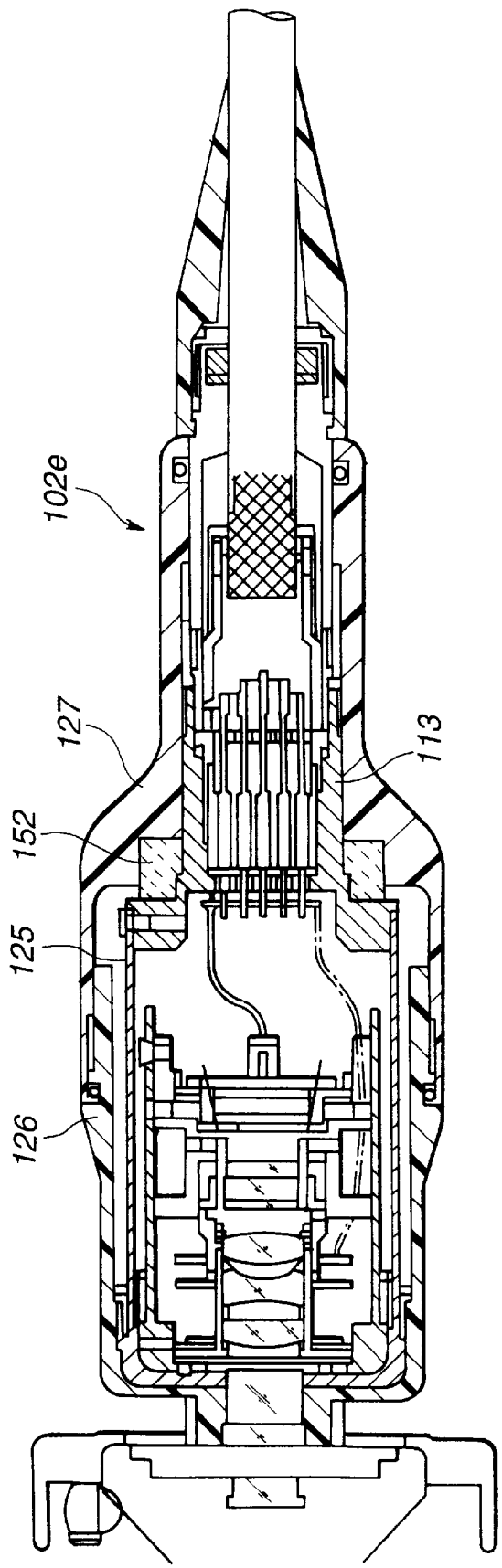
FIG. 18 is a sectional view of a camera head of a fifth variant of the fifth embodiment.

FIG. 18 shows a camera head 102e of a fifth variant of the fifth embodiment. The basic structure of the camera head 102e is identical to that of the first variant. Only the differences from the first variant will be described below.

In the camera head 102e, an elastic constraining member 152 realized as a rubber packing is interposed between the intra-head connector 113 and second insulation cover 127 shown in FIG. 13. The elastic constraining member 152 presses the intra-head connector 113 and second insulation cover 127 in the optical-axis and radial directions. The other components are identical to those of the first variant.

According to the foregoing structure, the same operations and advantages of the first and fourth variants are provided. Moreover, the elastic constraining member 152 can impose in the radial direction a constraining force on the insulating layer composed of the insulation covers 126 and 127, the shielding layer formed by the internal shielding sheathing 125, and the intra-head connector 113. A change in length of the insulating layer composed of the insulation covers 126 and 127, the shielding layer formed by the internal shielding sheathing 125, or the intra-head connector 113 deriving from a change in ambient temperature can therefore be effectively absorbed. Thus, optical precision can be fully ensured.

Figure 19:
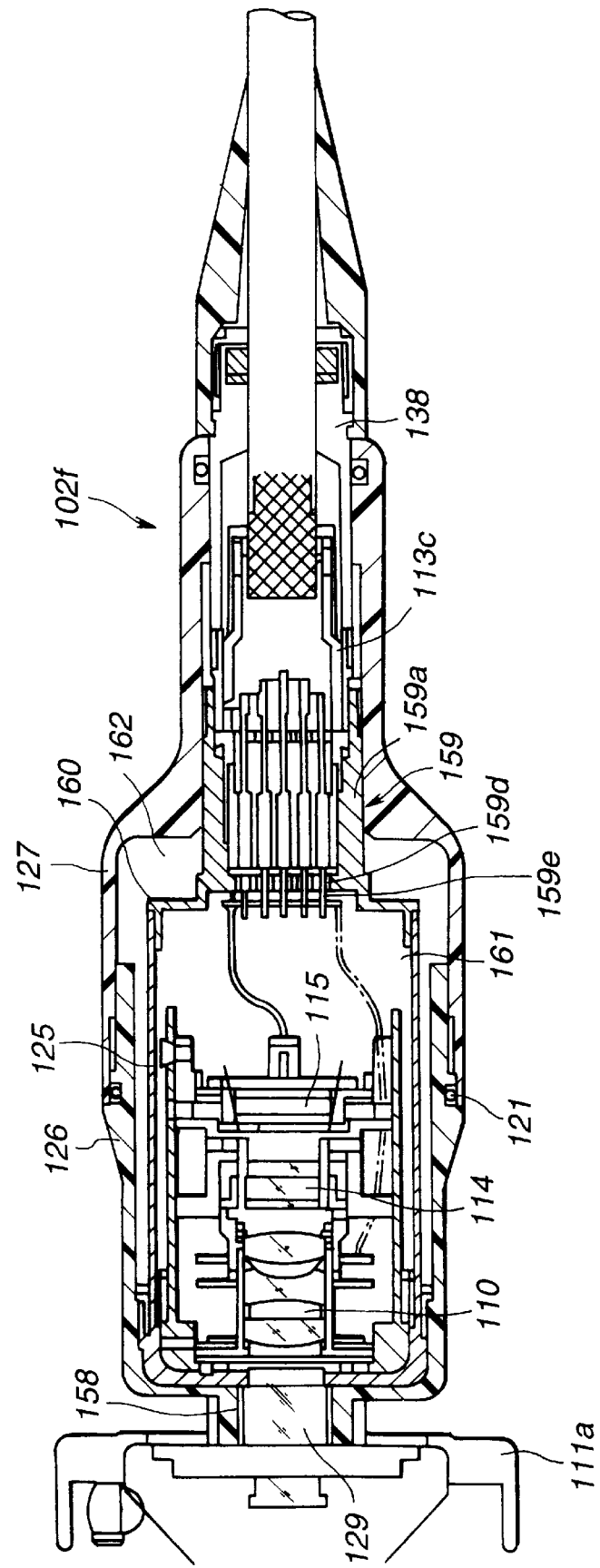
FIG. 19 is a sectional view of a camera head of a sixth variant of the fifth embodiment of the present invention.

FIG. 19 shows a camera head 102f of a most preferred variant of the fifth embodiment of the present invention. The basic structure of the camera head 102f of this embodiment is identical to that of the first variant. Only the differences from the first variant will be described below.

In the camera head 102f of this embodiment, the intra-head connector 113 of the first variant is formed as a hermetic connector 159. A hermetic plug 159a of the hermetic connector 159 and the internal shielding sheathing 125 are joined hermetically by a hermetic joint 160.

In other words, the hermetic joint 160 is realized by brazing or soldering the metallic frame of the hermetic plug 159a and the metallic internal shielding sheathing 125.

Moreover, the hermetic plug 159a is provided with solid contact pins 159e and a hermetic seal 159d for hermetically sealing the contact pins 159c and isolating them from their surroundings. Moreover, the outer circumference of the cover glass 129 is metallized. The internal shielding sheathing 125 and cover glass 129 are joined hermetically by a hermetic joint 158 that is realized by brazing or soldering the internal shielding sheathing 125 and cover glass 129.

Due to these components, a space defined by the cover glass 129, internal shielding sheathing 125, and hermetic plug 159a becomes a hermetic space 161 that remains airtight even during autoclaving.

Moreover, the first insulation cover 126 and second insulation cover 127 are placed outside a shielding layer composed of the internal shielding sheathing 125, hermetic connector 159, and connector cover 113c. The internal shielding sheathing 125 and first insulation cover 126 are joined in a watertight fashion by a watertight sealing member near the mount member 111a.

Consequently, due to these components, a watertight space 162 is defined by the internal shielding sheathing 125, insulation covers 126 and 127, and cable sealing frame 138. All the components of the camera head 102f are made of materials resistive to a temperature of at least 135° C. The other components are identical to those of the first variant.

According to the foregoing structure, the same operations and advantages as those of the first variant are provided. Moreover, when the camera head is autoclaved using high-temperature and high-pressure steam, at least the image formation optical system 110, filter unit 114, and imaging device 115 can be kept airtight.

Figure 20:
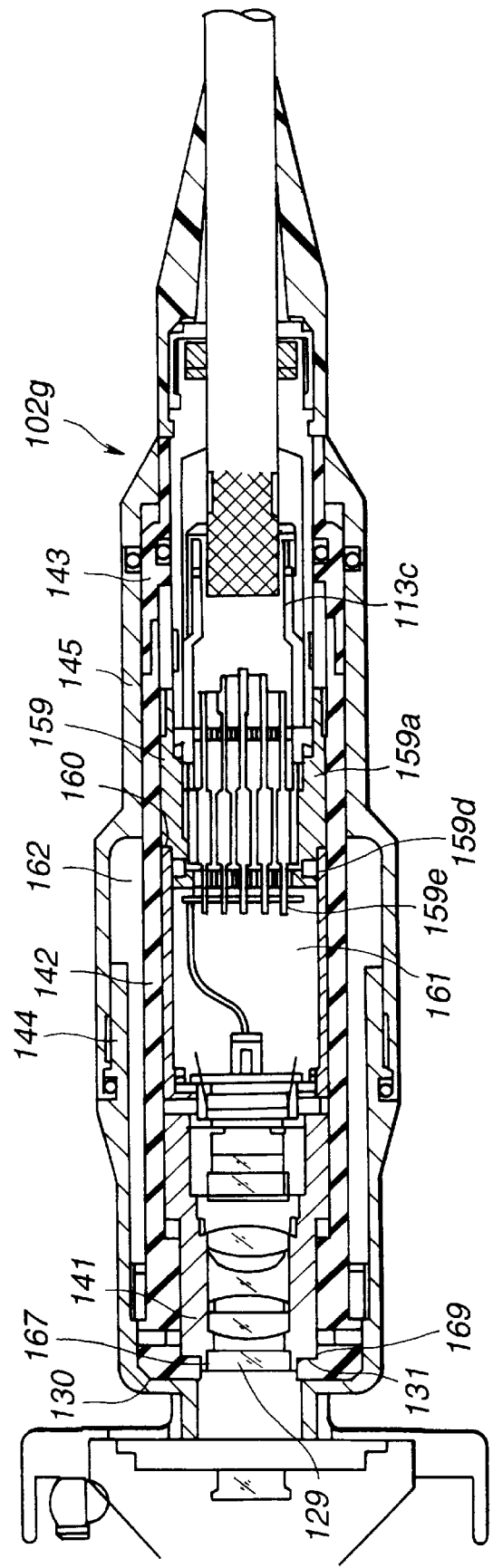
FIG. 20 is a sectional view of a camera head of a sixth embodiment of the present invention.

FIG. 20 shows a camera head 102g of a sixth embodiment of the present invention. The basic structure of the camera head 102g of this embodiment is identical to that of the second variant of the fifth embodiment. Only the differences from the second variant of the fifth embodiment will be described below.

In the camera head 102g of this embodiment, the hermetic plug 159a and optical bearing/shielding sheathing 141 are joined hermetically by the hermetic joint 160. The optical bearing/shielding sheathing 141 and cover glass 129 are joined hermetically by the hermetic joint 167.

A first insulation cover 142 and second insulation cover 143 are placed outside the optical bearing/shielding sheathing 141 and hermetic connector 159. A first housing metallic cover 144 and second housing metallic cover 145 are placed outside the first and second insulation covers. Moreover, the first housing metallic cover 144 and first insulation cover 142 are joined in a watertight fashion by the bumping member 131 to which a watertight sealant 169 is applied.

According to the foregoing structure, the same operations and advantages as those of the second variant of the fifth embodiment are provided.

Figure 21:
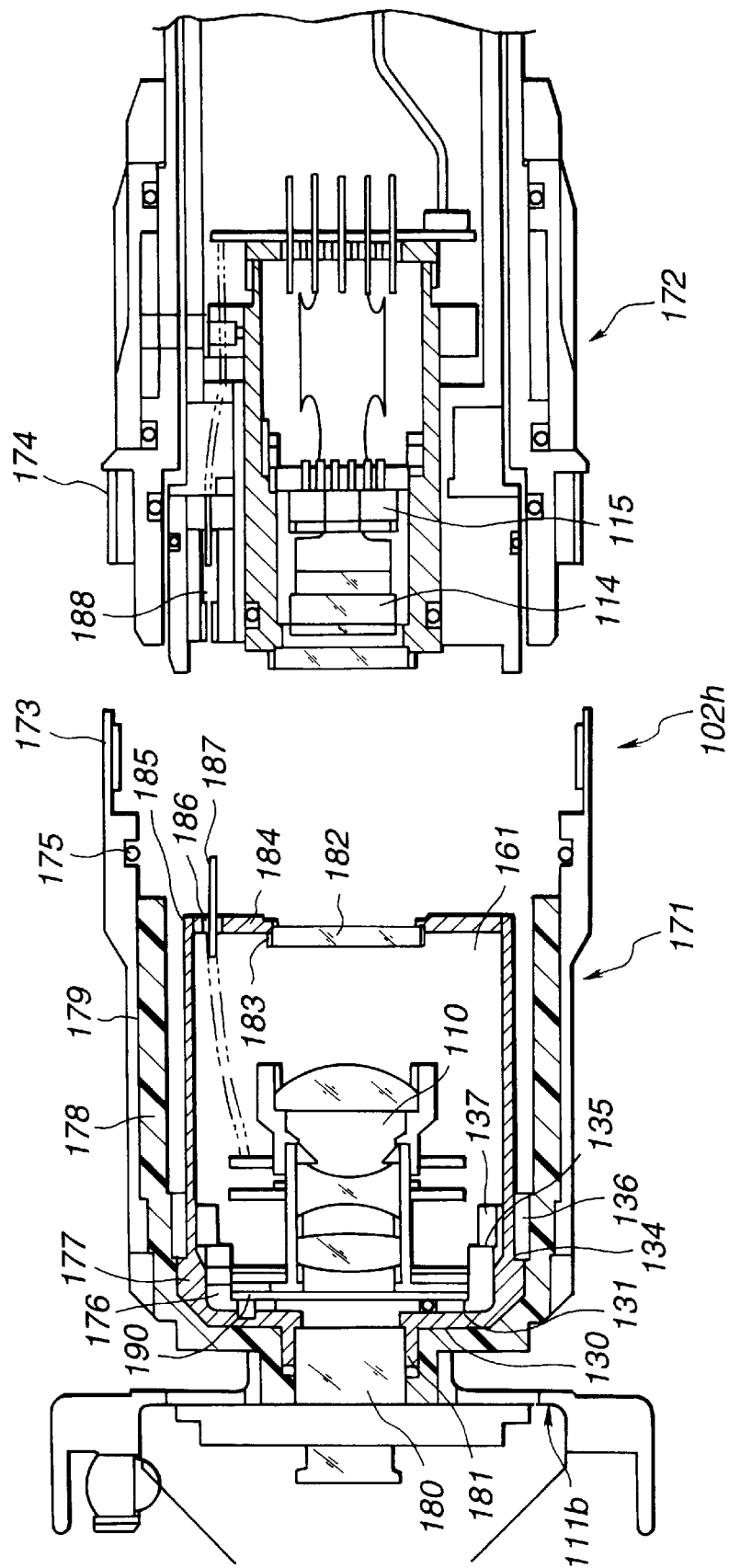
FIGS. 21 and 22 relate to a seventh embodiment of the present invention.
Figure 22:
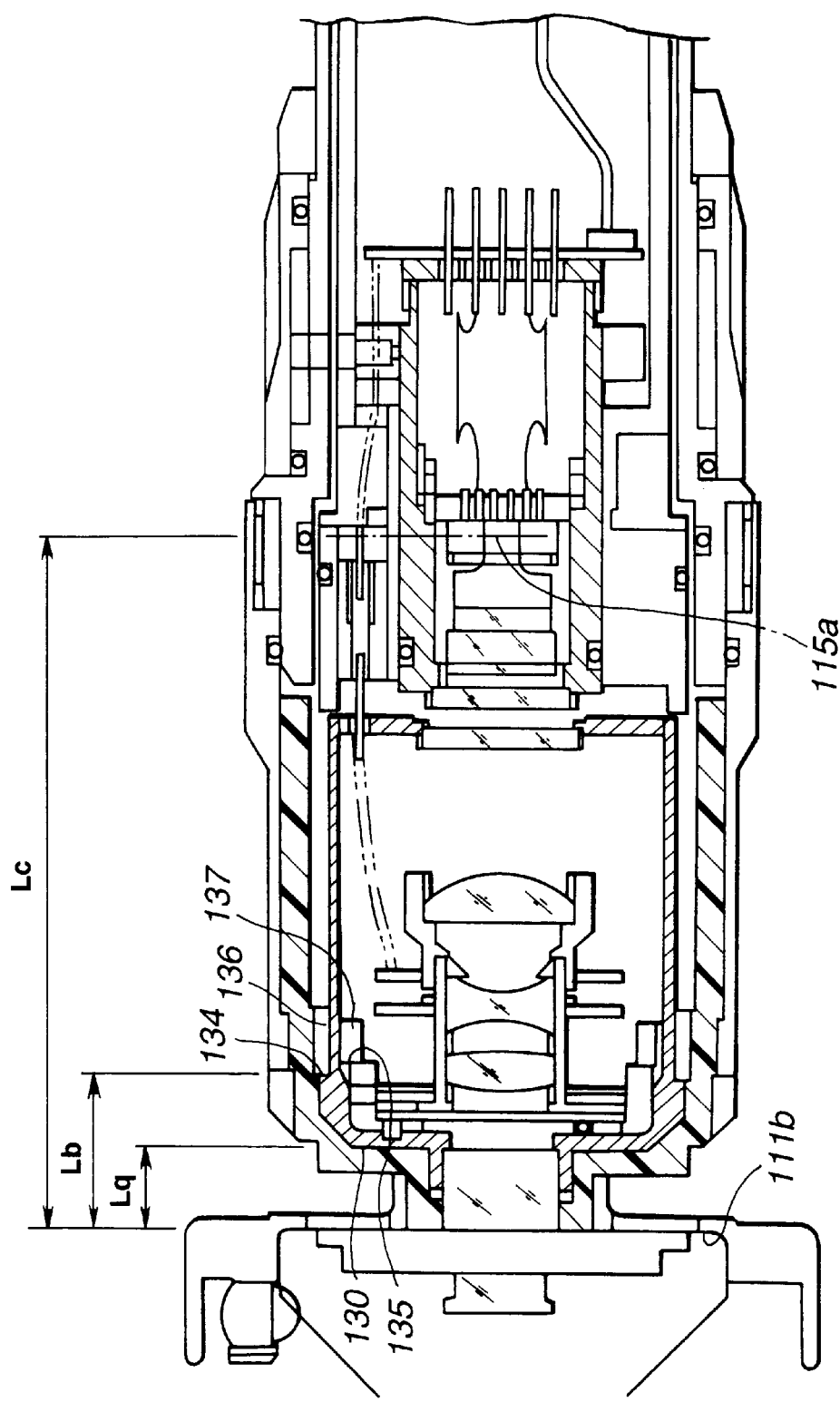

Referring to FIGS. 21 and 22, a camera head 102h of a seventh embodiment of the present invention will be described below. The basic structure of the camera head 102h of this embodiment is identical to that of the first variant of the fifth embodiment. Only the differences from the first variant will be described below.

The camera head 102h of this embodiment includes an optical adapter 171 including cover glasses 180 and 182 and an image formation optical system 110, and a camera head body 172 which is joined to the optical adapter 171 in a detachable manner and which includes a filter unit 114 and imaging device 115.

The optical adapter 171 has an imaging optical system incorporated therein, which is composed of a first cover glass 180, iris unit 190, image formation optical system 110, and second cover glass 182.

The image formation optical system 110 is formed as an integral part of the iris unit 190. The iris unit 190 is engaged with a lens bearing member 176. An internal shielding sheathing 177 is placed outside the lens bearing member 176. The internal shielding sheathing 177 and first cover glass 180 are joined hermetically by a hermetic joint 181.

Moreover, the end surface of the internal shielding sheathing 177 on the side of the camera head body 172 and a hermetic connector 184 are hermetically joined by a hermetic joint 185. The hermetic connector 184 and second cover glass 182 are hermetically joined by a hermetic joint 183. Moreover, the hermetic connector 184 is provided with a solid contact pin 187 and a hermetic seal 186 for hermetically isolating the contact pin 187 from the surroundings thereof.

According to the foregoing structure, a hermetic space 161 is defined by the first cover glass 180, internal shielding sheathing 177, hermetic connector 184, and second cover glass 182.

Moreover, an insulating sheathing 178 is placed outside the internal shielding sheathing 177. A connection ring 179 having a head mount 173, which is mountable on a head mount 174 of the camera head 172 in a freely dismountable fashion, and an elastic watertight member 175 are placed outside the insulating sheathing 178.

A contact receptor 188 is located on the camera head body 172 at a position at which the contact pin 187 is fitted into the contact receptor. Moreover, a head mount 174 is located on the camera head body 172 at a position at which the head mount 173 is engaged with the head mount.

The camera head 102h of this embodiment includes the iris unit 190. The iris unit 190 may be a stand-alone motor-driven unit (for example, a lens drive unit). When the iris unit 190 is not included, the image formation optical system 110 is supported by the lens bearing member 176. This alternative obviates the necessity to provide at least the hermetic seal 186, contact pin 187, and contact receptor 188. Moreover, the optical adapter 171 of the camera head 102h of this embodiment is structured to be airtight. Alternatively, the optical adapter may be structured to be watertight. The other components are identical to those of the first variant of the fifth embodiment.

According to the foregoing structure, the same operations and advantages as those of the first variant of the fifth embodiment are provided. Moreover, the optical adapter 171 and camera head body 172 can be freely detachably attached to each other via the head mounts 173 and 174 while airtightness (and watertightness) is ensured.

Moreover, the optical adapter 171 can be readily replaced with another. A plurality of different types of optical adapters 171, such as an optical adapter in which the image formation optical system 110 has a different focal distance, an optical adapter including a zoom lens or iris unit 190, or an optical adapter to which a motor-driven unit can be attached freely, for example, can each be used in combination with the camera head body described herein.

Next, an endoscope system including an eighth embodiment of the present invention will be described below. In the eighth embodiment, it is first determined whether the camera which includes a solid-state imaging device has been mounted on an endoscope using relay lenses for image transmitting or on an endoscope employing an image guide formed from a bundle of optical fibers. The camera head is then operated optimally according to the determined type of endoscope.

Figure 23:
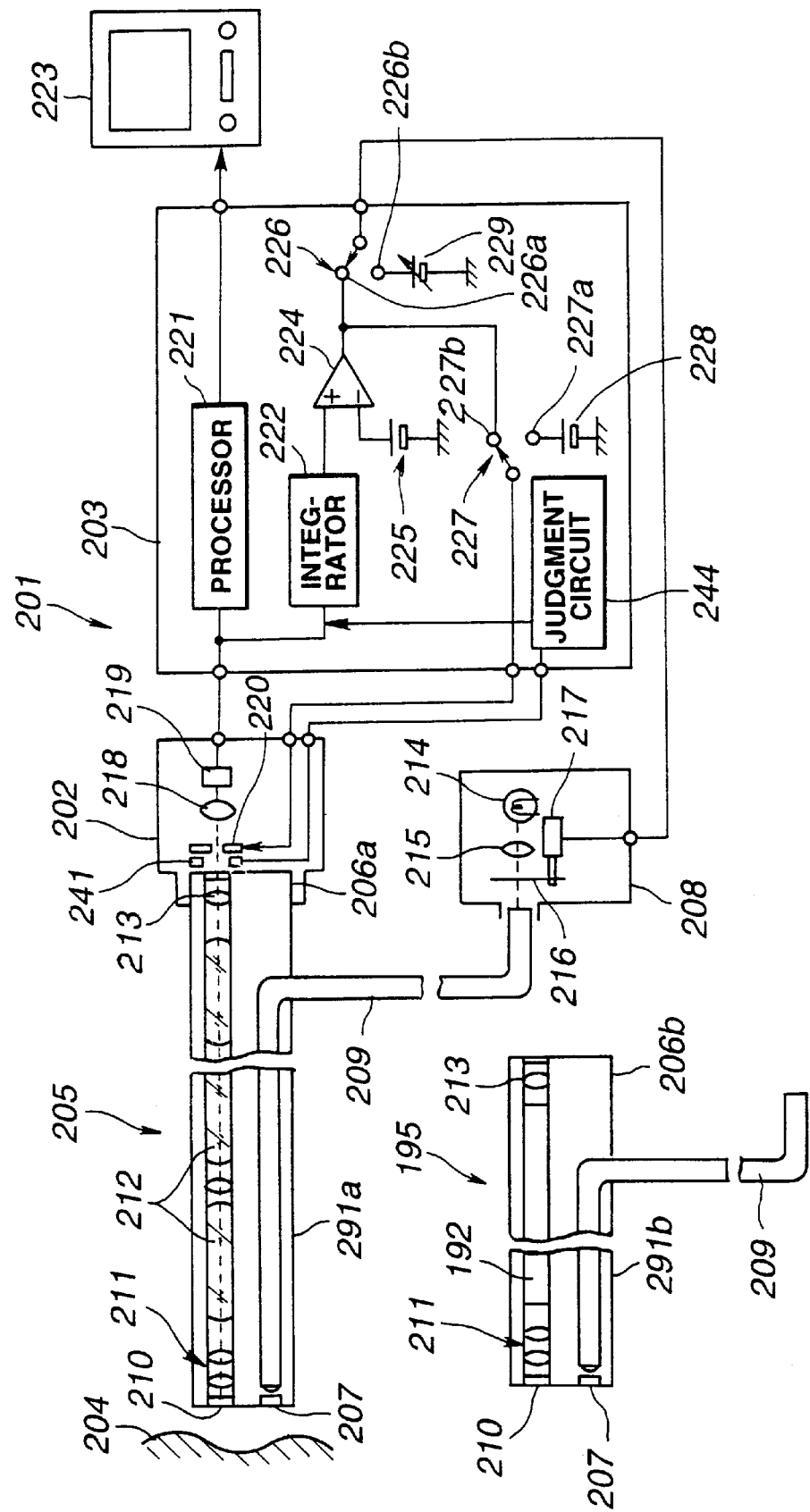
FIG. 23 is an explanatory diagram showing the schematic configuration of a mountable TV camera unit for endoscopes in accordance with an eighth embodiment of the present invention.

A mountable TV camera unit 201 for endoscopes shown in FIG. 23 comprises a camera head 202 and image signal processing unit 203. The camera head 202 is freely detachably attached to an eyepiece unit 206a of an endoscope, for example, a rigid endoscope 205 to be inserted into a body cavity for observation of an object 204 in the body cavity.

The camera head 202 of the TV camera unit 201 can also be freely detachably attached to an eyepiece unit 206b of a soft endoscope 195 employing an image guide (hereinafter IG) 192 formed from a bundle of optical fibers.

The camera head 202 of the TV camera unit 201 can be mounted on either of the eyepiece units 206a and 206b by selecting either the rigid endoscope 205 serving as a first endoscope and having a relay lens 212 and a rigid insertion unit 291a, or the soft endoscope 195 serving as a second endoscope and having an IG 192 and a soft insertion unit 291b.

The rigid endoscope 205 has an illumination lens 207 incorporated in the distal part of the insertion unit 291a. The object 204 is illuminated through the illumination lens 207. The rigid endoscope 205 further includes a light guide (hereinafter LG) 209 formed from a bundle of optical fibers over which illumination light emanating from a light source apparatus 208 is propagated, an observation window 210 through which light reflected from the object 204 and carrying an image of the object 204 is received and which is located at the distal end of the rigid endoscope 205, and a plurality of relay lenses 212 for propagating the reflected light incident on the observation window 210 to the eyepiece unit 206a through an objective 211. The light reflected from the object 204 passes through the relay lenses 212 and falls on the proximal surface of the eyepiece unit 206a through an eyepiece 213. Consequently, the image can be viewed.

On the other hand, the insertion unit 291b of the soft endoscope 195 to be introduced into a body cavity is flexible. The object 204 is illuminated through an illumination lens 207 incorporated in the distal part of the insertion unit 291b. The soft endoscope 195 includes an LG 209 for transmitting illumination light emanating from the shared light source apparatus 208; an observation window 210 through which light reflected from the object 204 and carrying an image of the object is received and which is located at the distal end of the soft endoscope; and an eyepiece 213 for re-forming the image carried by the reflected light incident on the observation window 210 on the distal surface of the IG 192 and via an objective 211, and for transmitting the image to the back end surface of the eyepiece unit 206b over the IG 192. Thus, the image can be viewed in enlargement through the eyepiece 213.

The light source apparatus 208 comprises, for example, a light source lamp 214 for supplying illumination light, and a condenser 215 for converging the illumination light emanating from the light source lamp 214 onto the proximal end surface of the LG 209 in the rigid endoscope 205 or soft endoscope 195. Aperture blades 216 for controlling an amount of illumination light supplied to the endoscope are placed between the condenser 215 and the proximal end surface of the LG 209. The aperture blades 216 are turned by a reversible motor 217 for controlling the aperture blades, whereby an amount of illumination light emanating from the light source lamp 214 and falling on the incident end surface of the LG 209 can be increased or decreased as necessary.

The camera head 202 comprises an imaging condenser 218 for converging reflected light to be introduced through the proximal end surface of the eyepiece unit 206a or 206b of the rigid endoscope 205 or soft endoscope 195, and an imaging device 219 for photoelectrically converting the reflected light converged by the imaging condenser 218. A diaphragm 220 for controlling or adjusting an amount of reflected light is disposed in the camera head 202 so as to be placed between the proximal end surface of the eyepiece unit 206a or 206b of the rigid endoscope 205 or soft endoscope 195 and the imaging condenser 218.

Figure 25A:
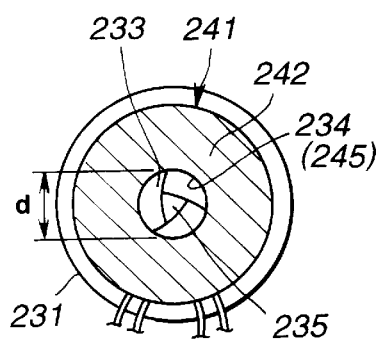
FIGS. 25A, 25B, and 25C are explanatory diagrams showing a diaphragm mechanism for the TV camera unit.
Figure 25B:
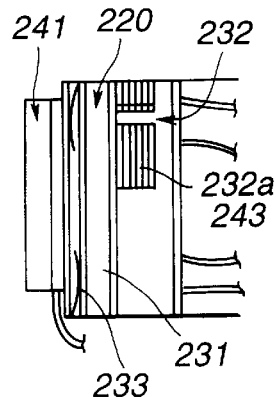
Figure 25C:
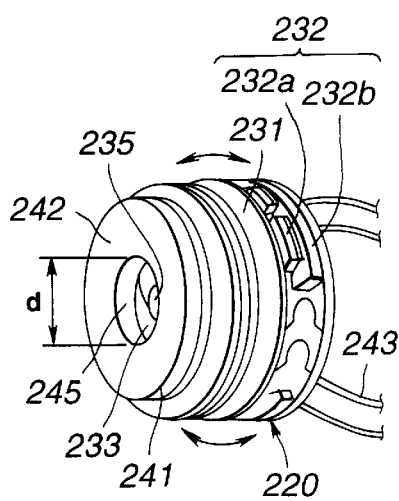

The diaphragm 220 is, as shown in FIGS. 25A, 25B, and 25C, formed with a rotary (iris) diaphragm mechanism for extending the depth of field. The rotary diaphragm mechanism has a plurality of aperture blades 233 which slide across one another when the rotary diaphragm mechanism is turned by a rotation driving source (drive coil 232a and permanent magnet 232b) 232, which is incorporated in a body case 231.

The body case 231 has a hollow 234 which provides a maximum aperture d and is formed in the optical-axis direction. The magnitude of an opening 235 is determined by controlling a number of rotations by which the aperture blades 233 are turned, using the rotation driving source 232. Thus, the opening can be set to a desired aperture. The maximum aperture d provided by the hollow 234 is substantially equal to the diameter of an entrance pupil provided in the rigid endoscope 205 employing the relay lenses 212. The aperture blades 233 are positioned substantially near the position of the entrance pupil defined by an area of light emitted from proximal end of the rigid endoscope 205. The actual diameter of the hollow 234 providing the maximum aperture d may be equal to or larger than the diameter of the entrance pupil, since the opening 235 can be set to any aperture less than its maximum.

Moreover, the diaphragm 220 is not limited to the rotary diaphragm mechanism (iris diaphragm mechanism), and may alternatively be a diaphragm mechanism used in a typical TV camera. For example, a guillotine-type diaphragm mechanism can be used. However, even when the guillotine-type diaphragm mechanism is employed, the setting must be the same as that for the rotary diaphragm mechanism. Specifically, the diameter of the hollow providing the maximum aperture, the magnitude by which the opening is opened by the aperture blades moved by the driving mechanism, and the positional relationship relative to the position of the entrance pupil must each be set in the same manner.

An image signal which has been photoelectrically converted by the imaging device 219 is transmitted to a processor 221 and integrator 222 incorporated in the image signal processing unit 203. The processor 221 uses the image signal to produce a video signal, for example, an NTSC signal so that an object image can be displayed on a viewing monitor 223.

The integrator 222 integrates components of the image signal photoelectrically converted by the imaging device 219, converts a resultant signal into a direct current (DC) signal, and thus produces a control signal for adjusting light. An output of the integrator 222 is input to a differential amplifier 224 through one input terminal (non-inverting input terminal). A reference voltage 225 is applied to the other input terminal (inverting input terminal) of the differential amplifier 224. Herein, the value of the reference voltage 225 is proportional to a target value of an amount of light to be controlled.

The image signal processing unit 203 is provided with switches 226 and 227. The switches 226 and 227 are, for example, manually changed over to different contacts and interlocked with each other. Specifically, when one switch 226 is set to an SW contact 226a, the other switch 227 is set to an SW contact 227a. When one switch 226 is set to an SW contact 226b, the other switch is set to an SW contact 227b. Thus, the switches are flipped while in interlocking relationship with each other.

When the SW contact 226a and SW contact 227a are selected, a given voltage 228 is applied to the SW contact 227a. Based on the given voltage 228, the opening 235 of the diaphragm 220 is forcibly locked in an open state. Based on an output of the differential amplifier 224, the reversible motor 217 for controlling the aperture blades is driven in order to turn the aperture blades 216. Thus, the amount of illumination light is controlled or adjusted until the output of the integrator 222 becomes substantially equal to the reference voltage 225. This state is referred to as a normal mode.

On the other hand, when the switches 226 and 227 are changed over to the SW contact 226b and SW contact 227b respectively, a variable voltage 229 is applied to the SW contact 226b. An output terminal of the differential amplifier 224 is connected to the SW contact 227b. The reversible motor 217 for controlling the aperture blades is driven with the variable voltage 229, whereby the aperture blades 216 are turned in order to control the amount of illumination light. Thus, the amount of illumination light is set to a maximum amount within a range in which the LG 209 provided in the rigid endoscope 205 or soft endoscope 195 will not be burnt. The magnitude by which the opening 235 of the diaphragm 220 is opened is adjusted according to an output of the differential amplifier 224. Thus, the output of the integrator 222 is substantially equalized to the reference voltage 225. This state is referred to as a large depth-of-field mode (also known as an AF mode).

Furthermore, the camera head 202 is provided with an optical sensor 241 that is located between the eyepiece unit 206a or 206b of the endoscope and the imaging condenser 218 and that is used to sense the type of endoscope mounted to the camera head. The optical sensor 241 is connected to a judgment circuit 244 incorporated in the image signal processing unit 203 via an optical sensor cable 243. The judgment circuit 244 is connected to the integrator 222.

Figure 24:
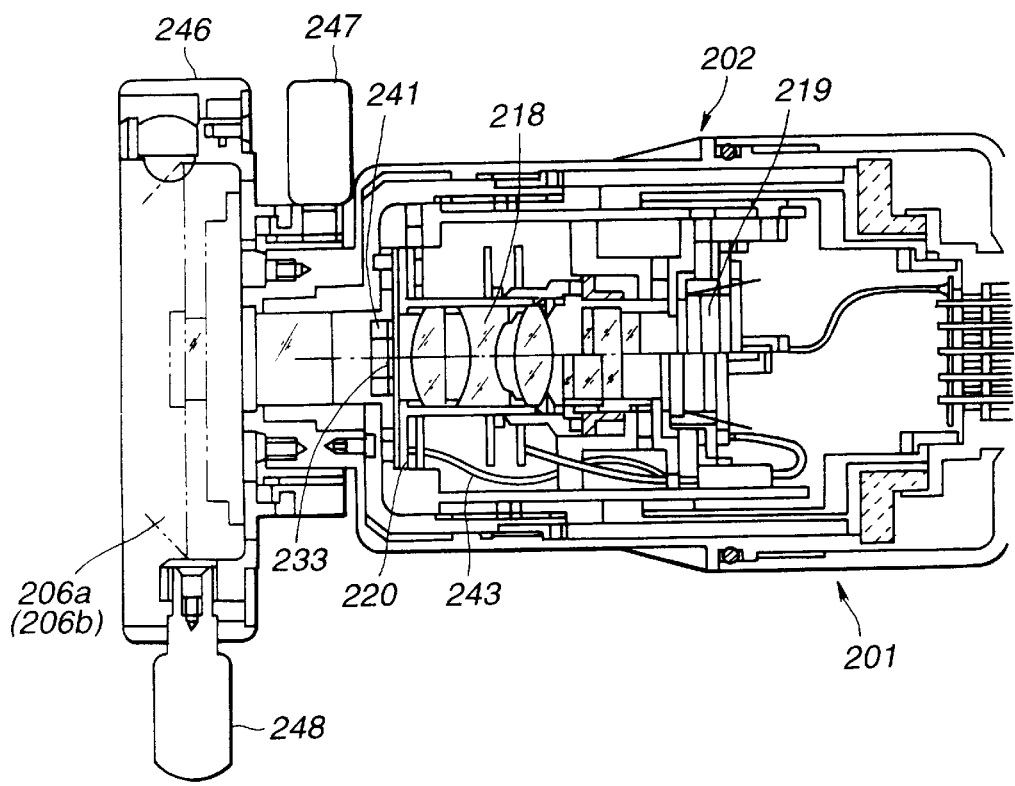
FIG. 24 is a longitudinal sectional view of the TV camera unit.

FIG. 24 is a longitudinal sectional view showing the camera head 202 in enlargement. The optical sensor 241 is attached to the front surface of a body case 231 (FIGS. 25A–25C) of the diaphragm 220. The light receiving surface 242 of the optical sensor 241 (hatched area in FIG. 25A) has a round shape to receive incident light coming from the eyepiece unit 206a or 206b.

The optical sensor 241 is formed with any of a photodiode, line sensor, and imaging device. The light receiving surface 242 has a hole 245 bored in the center thereof. The diameter of the hole 245 is equal to the diameter of the hollow 234 providing the maximum aperture.

In the present example, when the aperture blades 233 of the diaphragm 220 are opened to their greatest extent, the aperture is approximately 4 mm. This value is equivalent to the maximum value of the diameter of an entrance pupil produced by a locally procurable rigid endoscope. Moreover, incident light coming from the rigid endoscope 205 is a flux of substantially parallel rays in the vicinity of the light receiving surface 242 of the optical sensor 241. The amount of light received by the optical sensor 241 is therefore limited.

In the endoscope 195 having the IG 192 formed from a bundle of optical fibers, the diameter of a light beam is approximately 5 mm or more. The amount of scattered light is large; therefore, the amount of light received by the optical sensor 241 is also large. Based on the difference in the amount of light received by the light receiving surface 242 of the optical sensor 241, it can be determined with high precision whether the endoscope to which the camera head 202 is attached is the rigid endoscope 205 or the endoscope 195 having the IG 192.

In the camera head 202 of the TV camera unit 201, the mount 246 to be attached to the eyepiece unit 206a or 206b of an endoscope is of, for example, a bayonet coupling type and can therefore be readily attached, detached, or replaced with another. The main unit of the camera head 202 is provided with a lever 247 to be handled to attach or detach the mount 246. Moreover, the mount 246 is provided with a lever 248 to be handled to attach or detach the eyepiece unit 206a or 206b of the endoscope.

The camera head 202 shown in FIG. 24 has the optical sensor 241 incorporated in the structure of the camera 3 shown in FIG. 2.

Next, the operations of the mountable TV camera unit 201 for endoscopes having the foregoing structure will be described below.

First, an endoscope on which the mountable TV camera unit 201 is mounted for use is selected. The camera head 202 of the TV camera unit 201 is mounted on the endoscope. The light source apparatus 208 is then switched on. Light propagating through the eyepiece unit 206a or 206b of the endoscope falls on the camera head 202. An amount of light incident on the light receiving surface 242 of the optical sensor 241 is then detected. Otherwise, whether or not incident light is present is detected.

The detection signal is transmitted over the optical sensor cable 243 coupled to the optical sensor 241, and is sent to the judgment circuit 244 in the image signal processing unit 203 having the ability to control the camera. Based on the signal sent from the optical sensor 241, the judgment circuit 244 determines the type of endoscope on which the camera head 202 is mounted. In response to the determination by the sensing mechanism, the operations suitable for the endoscope on which the camera head 202 is mounted are carried out as described below.

FIG. 23 shows a configuration having the rigid endoscope 205 with the relay tenses 212. In this case, either the normal mode or large depth-of-field mode can be selected manually. An operator selects an optical mode according to a use situation and operates the TV camera unit accordingly.

First, the operations of the TV camera unit to be performed in the normal mode upon appropriate setting of the switches 226 and 227 of the image signal processing unit 203, will be described below. In the normal mode, illumination light emanating from the light source apparatus 208 is irradiated to the object 204 through the LG 209. Light reflected from the object 204 is propagated to the camera head 202 attached to the eyepiece unit 206a through the plurality of relay lenses 212.

The reflected light is converged on the end surface of the imaging device 219 by way of the opening 235 of the diaphragm 220 which has been brought to the open state, and of the imaging condenser 218. Photoelectric conversion is then carried out, thus producing an image signal. The processor 221 uses the image signal to produce a video signal and displays an object image on the viewing monitor 223. The image signal is also input to the integrator 222. The aperture blades 216 are turned so that a control signal resulting from integration performed by the integrator 222 will be equalized to the reference voltage 225. For turning the aperture blades 216, the reversible motor 217 drives the aperture blades according to an output of the differential amplifier 224. Thus, illumination light emanating from the light source lamp 214 and falling on the proximal end surface of the LG 209 is controlled. This enables successful observation under proper illumination.

In the alternate case, the switches 226 and 227 of the image signal processing unit 203 are changed over to the SW contact 226b and SW contact 227b, respectively. When the AF mode is selected, a maximum amount of illumination light irradiated from the light source apparatus 208 in response to the variable voltage 229. The maximum amount of illumination light is irradiated to the object 204 through the LG 209. Light reflected from the object 204 is propagated through the plurality of relay lenses 212 and transmitted to the camera head 202 attached to the eyepiece unit 206a.

The reflected light is converged on the end surface of the imaging device 219 by way of the diaphragm 220 and imaging condenser 218. The light is then photoelectrically converted into an image signal. The processor 221 uses the image signal to produce a video signal, and displays an object image on the viewing monitor 223. The image signal is also input to the integrator 222. The diaphragm 220 is controlled according to an output of the differential amplifier 224 so that a control signal resulting from integration performed by the integrator 222 will be equalized to the reference voltage 225. This process is essentially the same as that performed in an automatic focus mechanism.

In other words, as far as the typical imaging condenser is concerned, a larger "f" number represents to a larger depth of field. That is to say, if light of sufficient brightness falls on the imaging condenser, a larger "f" number set in the imaging optical system (a smallest possible aperture) leads to a larger depth of field. Consequently, the viewed object is irradiated with a maximum amount of light, and the amount of incident light is reduced by handling the diaphragm 220 according to the reference voltage 225. A large depth of field can be offered, wherein a high resolution can be attained for the whole viewing area ranging from a near point to a far point. The same effect as can be realized with an automatic focus mechanism can be attained with the present invention.

If a maximum amount of illumination light were irradiated to the LG 209 all the time, the LG 209 in some types of endoscopes might be damaged by heat. Even in this case, the switches 226 and 227 can be handled to change from the normal mode into the AF mode or vice versa. A large depth of field can be achieved if necessary, wherein a high resolution is attained over a large range of distances from a near point to a far point.

Next, the operations to be performed when the camera head 202 of the mountable TV camera unit 201 is mounted on the endoscope 195 with the IG 192 formed with a bundle of optical fibers will be described below. The eyepiece unit 206b of the endoscope 195 with the IG 192 is attached to the camera head 202. The light source apparatus 208 is then switched on. A portion of the rays falling on the camera head 202 through the eyepiece unit 206b of the endoscope 195 is incident on the light receiving surface 242 of the optical sensor 241. The light is then sensed by the optical sensor 241.

A detection signal sent from the optical sensor 241 is passed through the optical sensor cable 243, and sent to the judgment circuit 244 incorporated in the image signal processing unit 203. The judgment circuit 244 checks the signal sent from the optical sensor 241 to determine whether or not an endoscope attached to the camera head 202 is the IG-inclusive endoscope 195.

When the judgment circuit 244 determines that the endoscope attached to the camera head 202 is the IG-inclusive endoscope 195, a signal is sent to the integrator 222. An output of the differential amplifier 224 is used to stop the movement of the diaphragm 220. For example, the diaphragm 220 is locked in an open state in which the opening 235 of the diaphragm 220 opens to the greatest extent.

Specifically, when the switches 226 and 227 are changed over to the SW contact 226b and SW contact 227b respectively, the AF mode is set. Nevertheless, the diaphragm 220 is disabled from carrying out the automatic iris operation.

Even when the camera head 202 of the mountable TV camera unit 201 is mounted on the endoscope 195 with the IG formed with a bundle of optical fibers, unfavorable incidents can be avoided. Specifically, it can be avoided that a view image is vignetted, the perimeter of the view image gets darker, or the object cannot be observed. Moreover, irregularities in an image displayed on the monitor 223 due to interference between the array of fibers of the IG 192 and an array of pixels on a solid-state imaging device can be avoided. A satisfactory view of the image can thus be maintained.

Moreover, the locking of the diaphragm 220 is automatically activated. It is unnecessary for the user to handle a switch or the like or to seek the assistance of another for such purpose. Thus, the present invention provides convenience for the user while avoiding unfavorable incidents.

With the foregoing structure, a similar problem can be prevented from occurring in the endoscope 205 in which the entrance pupil is designed to be produced at a different position.

Incidentally, the diaphragm 220 is placed between the imaging condenser 218 and the proximal end surface of the eyepiece unit 206a and 206b. Alternatively, the diaphragm 220 may be placed along an optical path linking the image formation optical system and the imaging device 219 so that the amount of light incident on the imaging device 219 can be controlled. For example, the diaphragm 220 may be placed between the incidence surface of the camera head 202 and the imaging condenser 218.

Furthermore, in this embodiment, the judgment circuit 244 is connected to the integrator 222. As long as the movement of the diaphragm 220 can be stopped, an input cutoff switch may be placed in a circuit for supplying a signal to the diaphragm 220. The switch may be handled to carry out an input cutoff operation.

This embodiment can be adapted to a TV camera unit not including the switches 226 and 227 used to change modes.

Specifically, the configurations of the optical sensor 241 and judgment circuit 244 in this embodiment can be adapted to a TV camera unit not including the switches 226 and 227 used to change modes manually.

Figure 26:
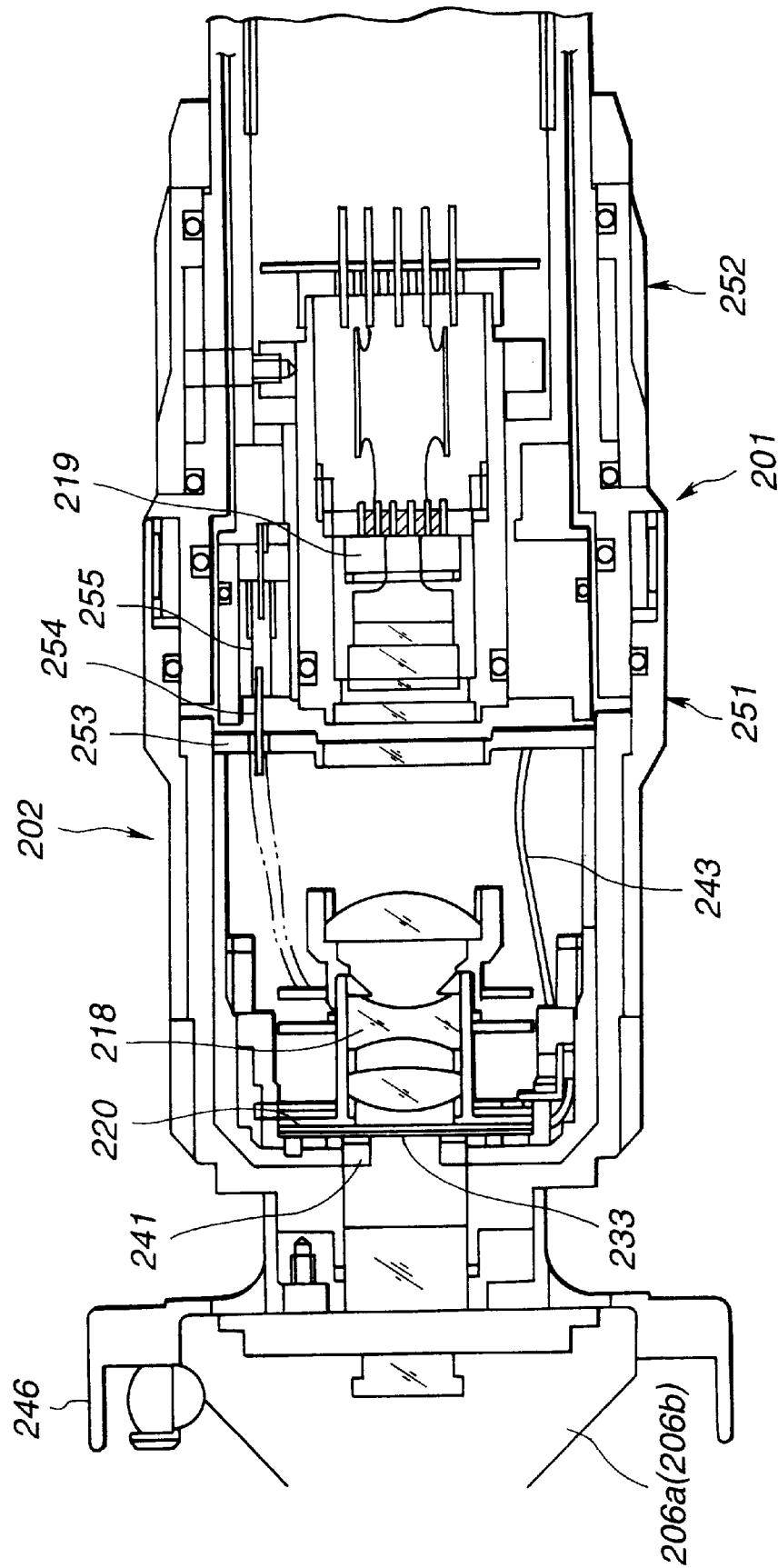
FIG. 26 is a longitudinal sectional view showing both an optical adapter and camera head body in accordance with a ninth embodiment of the present invention in a state in which they are attached to each other.
Figure 27:
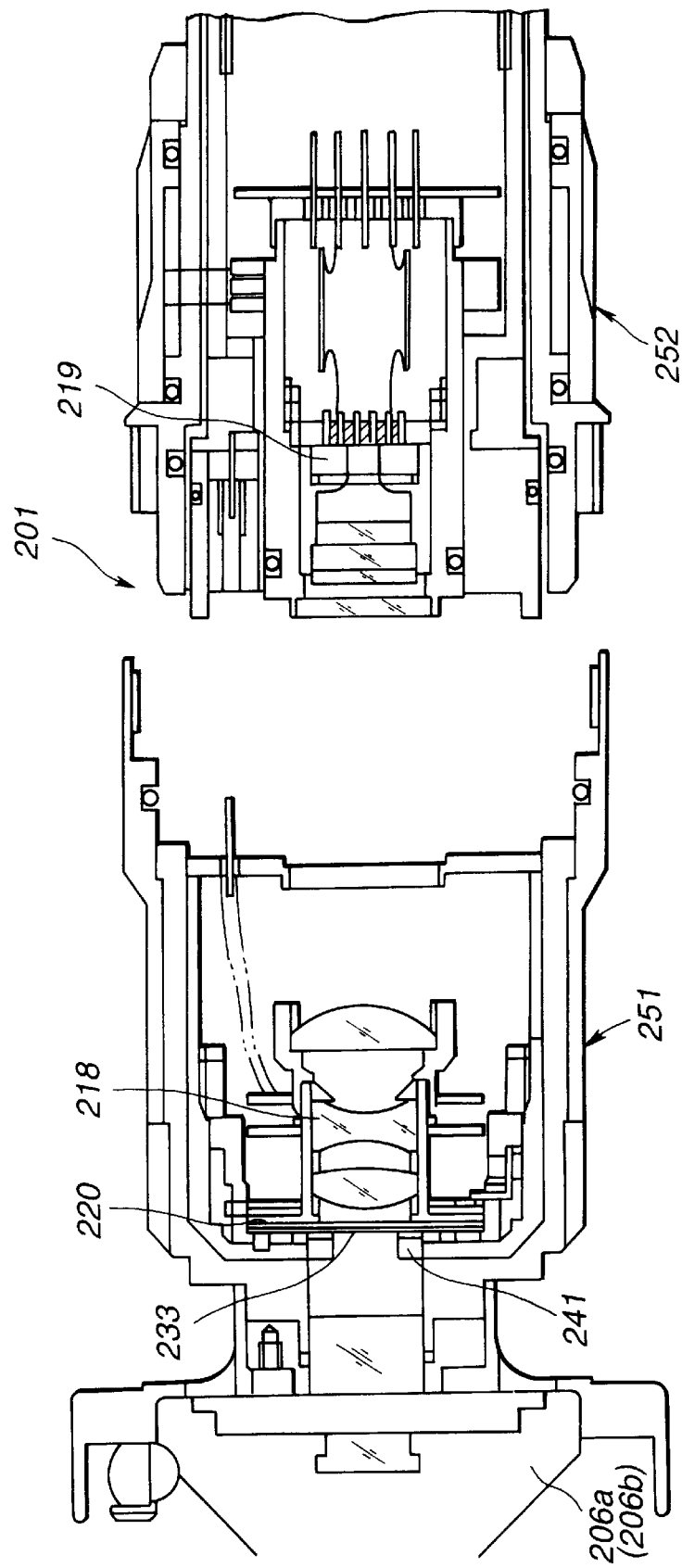
FIG. 27 is a longitudinal sectional view showing the optical adapter and camera head body in a state in which they are separated from each other.

Next, a ninth embodiment of the present invention will be described with reference to FIGS. 26 and 27.

The ninth embodiment is realized by dividing the eighth embodiment into two portions. The camera head 202 is divided into an optical adapter 251 and camera head body 252. The optical adapter 251 and camera head body 252 can be separated from each other as shown in FIG. 27.

Furthermore, the mount 246 to be attached to the eyepiece unit 206a or 206b of an endoscope is united with the optical adapter 251. Like the eighth embodiment, the mount may be designed to be able to be attached or detached or replaced with another.

The optical adapter 251 is, like the one of the eighth embodiment, provided with the optical sensor 241, diaphragm 220, imaging condenser 218, and optical sensor cable 243. The imaging device 219 and the like are incorporated in the camera head body 252. The optical adapter 251 is provided with an adapter connector 253 for electrically coupling the diaphragm 220 and optical sensor 241 to the camera head body 252. The adapter connector 253 has a plug 254. The plug 254 is fitted into a receptacle 255 in the camera head body 252.

According to the ninth embodiment, the imaging condenser 218 can be replaced with another through the camera head body 252. A plurality of optical adapters including an optical adapter offering a different focal distance and an optical adapter enabling a zoom function can be exchanged for the optical adapter 251. The other components are identical to those of the eighth embodiment.

Figure 28:
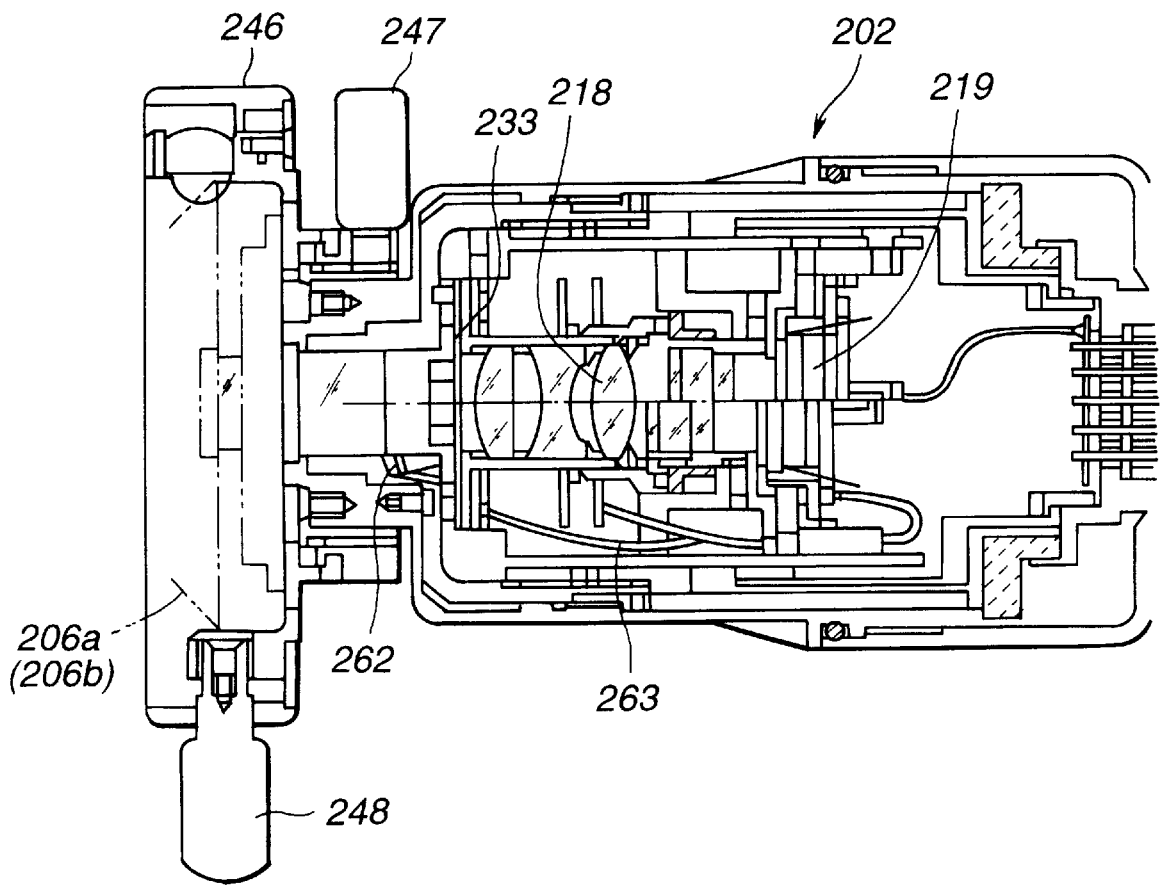
FIG. 28 is a longitudinal sectional view showing a camera head in accordance with a tenth embodiment.
Figure 29A:
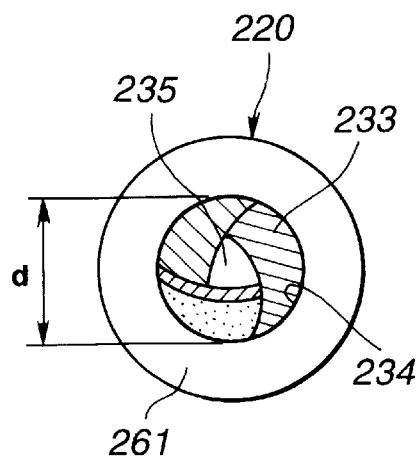
FIGS. 29A and 29B are explanatory diagrams showing both a diaphragm and an optical sensor.
Figure 29B:
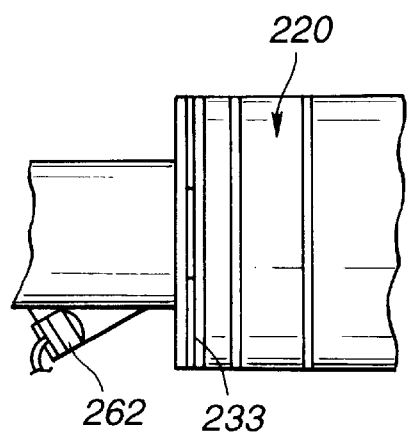

Next, a tenth embodiment of the present invention will be described with reference to FIGS. 28 and 29.

The basic structure of this embodiment is identical to that of the eighth embodiment. In the camera head 202, a sheet reflector 261 (FIG. 29A) is placed on the front surface of the diaphragm 220 located near the position of an entrance pupil formed by incident light coming from the rigid endoscope 205. An optical sensor 262 is located at a lateral position in front of the sheet reflector 261 so that the optical sensor will be opposed to the sheet reflector 261. The optical sensor 262 is connected to the judgment circuit 244 in the image signal processing unit 203 over an optical sensor cable 263.

Incidentally, a maximum aperture may be larger than the diameter of an entrance pupil produced by the rigid endoscope 205. In this case, the surface of at least part of the aperture blades of the diaphragm 220 may be used as a sheet reflector 261.

The operations of the tenth embodiment are fundamentally identical to those of the eighth embodiment. In this embodiment, incident light coming from the rigid endoscope 205 is restricted by the opening 235 of the diaphragm 220 located near the position of the entrance pupil. When no areas on the sheet reflector 261 have been irradiated, the optical sensor 262 will not produce any signal. However, when the camera head is attached to the endoscope with the image guide, light is irradiated to the sheet reflector 261. The light is sensed by the optical sensor 262. A signal sent over the optical sensor cable 263 is sent to the judgment circuit 244. Consequently, the camera unit senses that it has been mounted on the endoscope with the IG formed with a bundle of optical fibers.

Incidentally, when a maximum aperture is larger than the diameter of an entrance pupil, the level of light incident on the sheet reflector 261 or on a portion of the sheet reflector is sensed for determination. The other operations are all identical to those of the eighth embodiment.

According to this embodiment, compared with the eighth embodiment, the optical sensor can be designed more compactly. Moreover, the optical sensor located in front of the diaphragm 220 occupies a minimum amount of volume. This results in a compact design for the whole camera unit.

Moreover, in both the tenth and the eighth described embodiments, a locally procurable iris unit whose aperture is larger than the diameter of an entrance pupil can be used.

Next, an eleventh embodiment of the present invention will be described with reference to FIG. 30.

Figure 30:
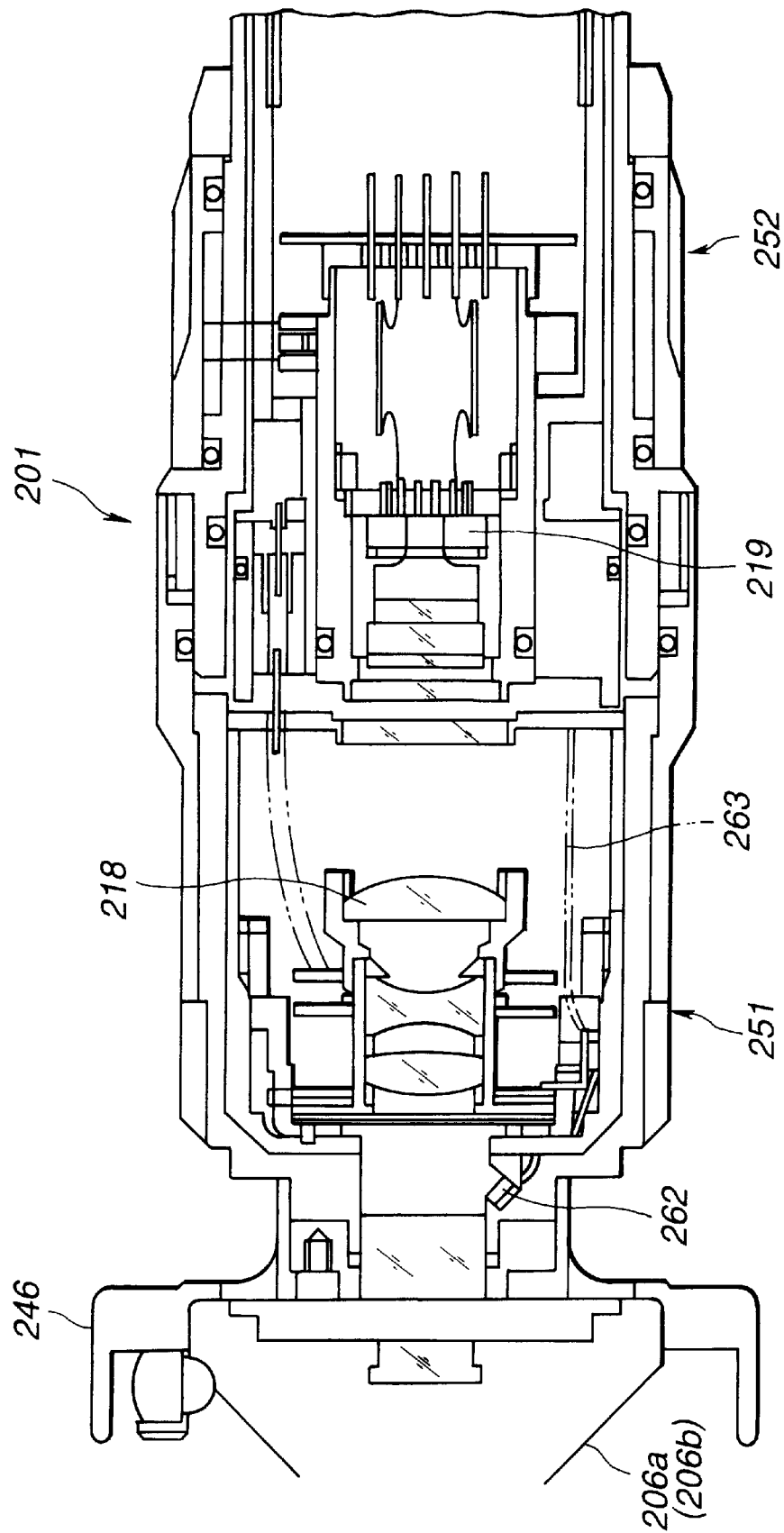
FIG. 30 is a longitudinal sectional view showing an optical adapter and camera head in accordance with an eleventh embodiment.

As shown in FIG. 30, this embodiment is realized by combining the structure of the ninth embodiment, in which the optical adapter 251 to be attached to the camera head 252 is replaced with the optical adapter of the tenth embodiment characterized by the structure and position of the optical sensor 262.

The operations and advantages of the eleventh embodiment are identical to those of the ninth and tenth embodiments.

Next, a twelfth embodiment of the present invention will be described with reference to FIG. 31.

In this embodiment, the basic components except the rigid endoscope 205 or IG-inclusive endoscope 195 and the camera head 202 are identical to those of the eighth embodiment.

Figure 31:
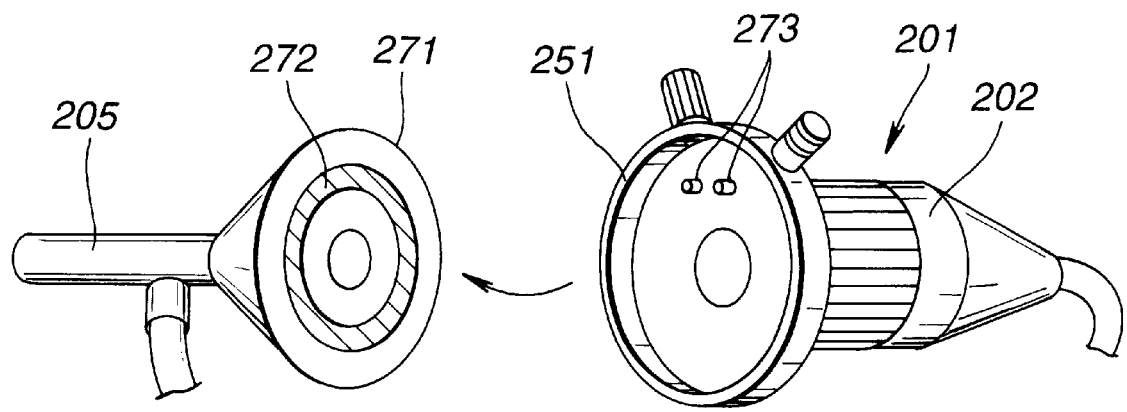
FIG. 31 is an oblique view showing a camera head in accordance with a twelfth embodiment and an eyepiece unit of an endoscope.

As shown in FIG. 31, in this embodiment, an annular metallic chip 272 is placed on the end surface of the eyepiece unit 271 of one of the IG-inclusive endoscope 195 and the rigid endoscope 205. Sensing contact pins 273 are formed on the optical adapter 205 of the camera head 202 in accordance with the diameter of the annular metallic chip 272.

The sensing contact pins 273 contact the metallic chip 272 when the camera head 202 is attached to the eyepiece unit 271 of the IG-inclusive endoscope 195 or the rigid endoscope 205. The sensing contact pins function as sensors for ascertaining the type of endoscope attached.

Thus, this embodiment provides a sensing mechanism for distinguishing an endoscope with the metallic chip 272 from an endoscope without the metallic chip 272.

The sensing contact pins 273 are connected to the judgment circuit 244 in the image signal processing unit 203 over a signal line that is not shown. The metallic chip 272 may be placed on the rigid endoscope 205 or the IG-inclusive endoscope 195. However, the metallic chip 272 is differentiated between the rigid endoscope 205 and the IG-inclusive endoscope 195.

Incidentally, the eyepiece unit of the endoscope is made of insulating materials except the metallic chip 272.

Assume that the rigid endoscope 205 or IG-inclusive endoscope 195 is attached to the camera head 202, and that the attached endoscope has the metallic chip 272. In this case, the sensing contact pins 273 contact the metallic chip 272 to enable electrical conduction therebetween. In contrast, if the attached endoscope does not have a metallic chip 272, the sensing contact pins 273 contact the eyepiece 271 but do not conduct; consequently, the judgment circuit 244 does not operate. Alternatively, the judgment circuit 244 may operate when the sensing contact pins do not conduct.

The fundamental advantages of this embodiment are identical to those of the eighth embodiment. Furthermore, the optical sensor is unnecessary, thereby simplifying the structure of the camera head. Moreover, strict alignment between the camera head and the eyepiece becomes unnecessary.

Next, a thirteenth embodiment of the present invention will be described with reference to FIG. 32.

The basic of this embodiment is identical to that of the eighth embodiment, except for slight modifications to the rigid endoscope 205 or IG-inclusive endoscope 195 and the camera head 202.

Figure 32:
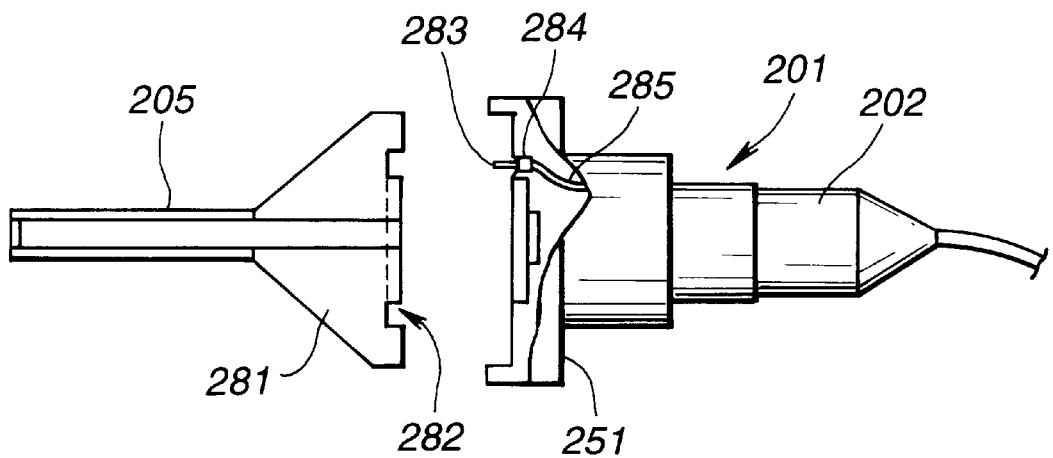
FIG. 32 is an explanatory diagram showing a camera head in accordance with a thirteenth embodiment and an eyepiece unit of an endoscope.

As shown in FIG. 32, in this embodiment, the eyepiece unit 281 of one of the IG-inclusive endoscope 195 and the rigid endoscope 205 is provided with an annular judgment step 282. Correspondingly, the optical adapter 251 of the camera head 202 is provided with a sensing switch 284 serving as a sensor for ascertaining a type of endoscope attached thereto and including a sensing contact pin 283. The sensing contact pin 283 is located at a position at which it comes into contact with the judgment step 282 when the eyepiece unit 281 of the IG-inclusive endoscope or rigid endoscope is attached to the camera head 202.

The sensing switch 284 is connected to the judgment circuit 244 in the image signal processing unit 203 over a signal line 285. Thus, the present embodiment provides a sensing mechanism for distinguishing an endoscope having the judgment step 282 from an endoscope not having a judgment step 282 as described herein. The judgment step 282 may be concave or convex.

Assume that the eyepiece unit 281 of the rigid endoscope 205 or the image guide-inclusive endoscope 195 is attached to the camera head 202, and that the attached endoscope has a concave judgment step 282. In this case, the sensing contact pin 283 remains in a protruding state from the surface of the camera head 202. Thus, the sensing switch 284 remains in the off position, and the judgment circuit 244 does not operate. In contrast, if the attached endoscope does not have concave judgment step 282, the sensing contact pin 283 is pressed inward toward the sensing switch 284. The sensing switch 284 is therefore turned on, causing the judgment circuit 244 to operate.

The above operation is identical when a convex judgment step 282 is provided in lieu of the concave step. Alternatively, the judgment circuit 244 may be configured to operate when the sensing switch 284 is turned off rather than on.

The advantages of this embodiment are identical to those of the twelfth embodiment. Additionally, the material of the eyepiece unit of an endoscope is not limited to any specific type. Specifically, it is not necessary to provide a metallic chip or the like.

As described so far, according to the eighth to thirteenth embodiments, the camera head is capable of automatically determining whether an attached endoscope is an endoscope having relay lenses incorporated therein or an endoscope having an image guide formed with a bundle of optical fibers. Restriction of the aperture is then appropriately executed or terminated automatically without requiring the user to handle any switches or the like. Consequently, it is unnecessary for the user to manually handle the diaphragm mechanism by himself/herself or to seek the assistance of others whenever the endoscope must be replaced with another during surgery. The present invention is thus quite convenient to use.

The present invention may be embodied in other specific forms without departing from the spirit or essential attributes thereof and, accordingly, reference should be made to the appended claims, rather than to the foregoing specification, as indicating the scope of the invention.

What is claimed is:

1. An endoscopic imaging apparatus, comprising:

an outer metallic sheathing including a mount which is attachable to an eyepiece unit of an endoscope, said outer metallic sheathing forming a first housing member having a first opening adapted to be positioned opposing the eyepiece unit, a second opening, and substantially defining a storage space which remains airtight during autoclaving;

an optical system aligned with said first opening of said first housing member so as to be opposed to said eyepiece unit, said optical system including at least an optical member located at said first opening to partially define said storage space;

a first seal for hermetically sealing said first opening in cooperation with said optical member included in said optical system so that said optical system can withstand autoclaving;

a solid-state imaging device disposed in said storage space and including a photoelectric converting mechanism located at a position at which an image produced by said optical system is formed;

a first electrical connector affixed in said second opening of said first housing member, said first electrical connector including a metallic connector frame and a plurality of first electrical contact pins which are electrically coupled to said solid-state imaging device via a corresponding first plurality of signal lines, said first electrical connector being hermetically sealed using an insulating hermetic member so that said first electrical contact pins can withstand autoclaving;

a second electrical connector having a plurality of second electrical contact pins which can be spliced to said plurality of first electrical contact pins;

an electrical cable formed from a second plurality of signal lines, wherein each of said second electrical contact pins are electrically coupled to one end of a corresponding second signal line, said electrical cable being surrounded with a shielding sheath which in turn is protected by an insulating sheath;

a second housing member made from an insulating material and adapted to be coupled to said first housing member in a water-tight manner so as to shield said first electrical connector and said second electrical connector including said plurality of second electrical contact pins and said ends of said second signal lines forming said electrical cable to which said second electrical contact pins are electrically coupled;

an internal shielding sheathing placed inside said outer metallic sheathing and forming a conductive shielding layer;

an inner insulating sheathing placed between said outer metallic sheathing and said internal shielding sheathing and forming an insulating layer for isolating said outer metallic sheathing from said internal shielding sheathing;

an insulating element for isolating said outer metallic sheathing from said metallic connector frame inside said insulating second house member;

a second seal for hermetically sealing said insulating element so that said insulating element can withstand autoclaving; and a shielding member for enabling electrical communication to travel from said internal shielding sheathing through said metallic connector frame and to said shielding sheath, and vice versa, said shielding member shielding said second electrical connector.

2. An endoscopic imaging apparatus according to claim 1, wherein said insulating element is a ceramic member and has a first engagement surface for engaging said second opening of said outer metallic sheathing, and a second engagement surface for engaging an opening of said metallic connector frame, said first and second surfaces being metallized along respective portions thereof which engage said outer metallic sheathing and said metallic connector frame, and wherein said second seal is a hermetic binder for hermetically sealing the metallized portions of said first and second engagement surfaces of said ceramic member to said outer metallic sheathing and said metallic connector frame, respectively.

3. An endoscopic imaging apparatus according to claim 2, wherein said metallized portions are metallized using a metal with a nickel base, a metal with a cobalt base, a metal with a gold base, or a metal with a molybdenum-manganese alloy base.

4. An endoscopic imaging apparatus according to claim 2, wherein said hermetic binder is a brazing filler with a gold base, a brazing filler with a silver base, a solder with a tin-palladium alloy base, a low-fusing point glass, or an inorganic binder.

5. An endoscopic imaging apparatus according to claim 2, wherein said hermetic binder has a different fusing point at the location at which it hermetically seals said metallized portion of said first engagement surface and said outer metallic sheathing than the fusing point at the location at which it hermetically seals said metallized portion of said second engagement surface and said metallic connector frame.

6. An endoscopic imaging apparatus according to claim 1, wherein said metallic connector frame includes a disk portion having a plurality of bores therethrough, said plurality of first electrical contact pins each penetrating through a corresponding one of said bores, and wherein said insulating hermetic member is a hermetic sealing member formed from a glass-sintered body for sealing said plurality of first electrical contact pins penetrating through said bores.

7. An endoscopic imaging apparatus according to claim 1, wherein said optical member has a metallized engagement surface for engaging said first opening, and wherein said first seal for hermetically sealing said first opening is a hermetic binder for sealing said metallized engagement surface of said optical member and said first opening of said outer metallic sheathing.

8. An endoscopic imaging apparatus according to claim 1, wherein said endoscopic imaging apparatus is capable of remaining airtight and watertight during an autoclaving process in which said endoscopic imaging apparatus is exposed to steam of a temperature ranging from 121 to 135° and a pressure ranging from 1.5 to 2.2 atm for about 5 to 20 min.

9. An endoscopic imaging apparatus according to claim 1, wherein said shielding member is a frame for shielding at least the distal end of said electrical cable, said frame having an opening which is electrically coupled to an opening of said metallic connector frame.

10. An endoscopic imaging apparatus comprising:

a housing member including a mount to be attached to an eyepiece unit of an endoscope, and having a stowage space which remains airtight during autoclaving where sterilization is achieved under high-temperature and high-pressure steam defined therein;

an imaging optical system hermetically locked in a first opening of said housing member which is opposed to said eyepiece unit;

a solid-state imaging device stowed in said stowage space and provided with a photoelectric conversion mechanism located at a position at which an image produced by said imagine optical system is formed;

an electric connector hermetically locked in a second opening of said housing member, and including a metallic connector frame that has electric contact pins, which are electrically coupled to said solid-state imaging device over a plurality of signal lines, hermetically sealed with an insulating sealing member so that said electric contact pins can withstand autoclaving; and a sheathing structure outlining said housing member, said sheathing structure including a plurality of sheathing members for shielding said imaging optical system from outside, said sheathing structure further having linkage fixtures, which link said plurality of sheathing members gathered in the distal part of said endoscopic imagine apparatus which is located on the side of said endoscope beyond the plane of said solid-state imaging device, wherein said sheathing structure includes a conductive internal shielding sheathing for sheathing an electrical circuit that includes at least said solid-state imaging device, an optical support member for supporting said imaging optical system, and an insulating sheathing made of an insulating material for shielding said internal shielding sheathing and said optical support member.

11. An endoscopic imaging apparatus comprising:

a housing member including a mount to be attached to an eyepiece unit of an endoscope, and having a stowage space, which remains airtight during autoclaving where sterilization is achieved under high-temperature and high-pressure steam defined therein;

an imaging optical system hermetically locked in a first opening of said housing member which is opposed to said eyepiece unit;

a solid-state imaging device stowed in said stowage space and provided with a photoelectric conversion mechanism located at a position at which an image produced by said imaging optical system is formed;

an electric connector hermetically locked in a second opening of said housing member, and including a metallic connector frame that has electric contact pins which are electrically coupled to said solid-state imagine device over a plurality of signal lines, hermetically sealed with an insulating sealing member so that said electric contact pins can withstand autoclaving; and a sheathing structure outlining said housing member, said sheathing structure including a plurality of sheathing members for shielding said imaging optical system from outside, said sheathing structure further having linkage fixtures, which link said plurality of sheathing members gathered in the distal part of said endoscopic imaging apparatus which is located on the side of said endoscope beyond the plane of said solid-state imaging device, wherein said sheathing structure further includes an outer metallic sheathing for shielding said insulating sheathing.

* * * * *